United States Patent [19]

Minagawa et al.

[11] Patent Number: 4,468,488
[45] Date of Patent: Aug. 28, 1984

[54] POLY(PIPERIDYLAMINE) ALKANES AND SYNTHETIC RESIN COMPOSITIONS STABILIZED THEREBY

[75] Inventors: Motonobu Minagawa, Koshigaya; Yutaka Nakahara, Iwatsuki; Toshihiro Shibata, Omiya; Ryozo Arata, Urawa, all of Japan

[73] Assignee: Adeka Argus Chemical Co., Ltd., Urawa, Japan

[21] Appl. No.: 470,103

[22] Filed: Feb. 28, 1983

[30] Foreign Application Priority Data

May 7, 1982 [JP] Japan ................................ 57-76430

[51] Int. Cl.$^3$ ........................ C08K 5/34; C08L 25/06; C07D 401/14; C07D 401/12
[52] U.S. Cl. ..................................... 524/99; 524/100; 524/102; 524/103; 544/198; 544/209; 544/212; 546/187; 546/190; 546/210
[58] Field of Search ................. 524/100, 102, 103, 91; 546/187, 190, 210, 244; 544/198, 209, 212

[56] References Cited

U.S. PATENT DOCUMENTS

| | | | |
|---|---|---|---|
| 4,256,627 | 3/1981 | Moser et al. | 524/100 |
| 4,263,434 | 4/1981 | Cassandrine et al. | 544/198 |
| 4,321,374 | 3/1982 | Morimura et al. | 524/100 |
| 4,369,321 | 1/1983 | Cantatore | 546/197 |

FOREIGN PATENT DOCUMENTS 0014683  8/1980  European Pat. Off. .

*Primary Examiner*—John Kight, III
*Assistant Examiner*—Garnette D. Draper

[57] ABSTRACT

Poly(piperidylamine) alkanes represented by the Formula (I) or (II):

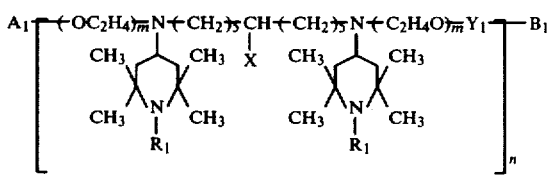

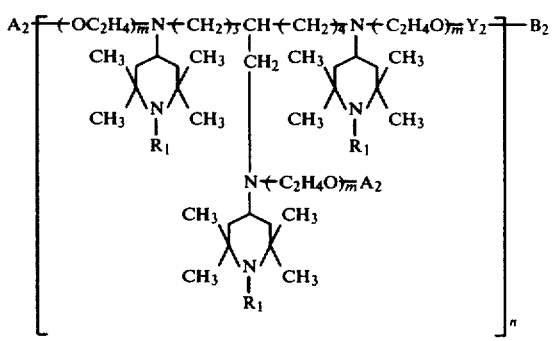

and synthetic resin compositions having improved resistance to deterioration by light containing such compounds.

30 Claims, No Drawings

POLY(PIPERIDYLAMINE) ALKANES AND SYNTHETIC RESIN COMPOSITIONS STABILIZED THEREBY

The 2,2,6,6-tetraalkylpiperidine compounds are known as light stabilizers for organic substances including synthetic polymers such as polyolefins, polyurethanes and styrene resins. Various types of 2,2,6,6-tetraalkyl-4-piperidyl amines are known.

Japanese Patent No. 80-7861 discloses 1-substituted-2,2,6,6-tetraalkyl-4-piperidyl amine derivatives such as N,N'-bis(1,2,2,6,6-pentamethyl-4-piperidyl) ethylene diamine.

U.S. Pat. No. 4,086,204, patented Apr. 25, 1978, provides tetraalkyl piperidine radical-containing polytriazine compounds produced by reacting a dihalogen triazine with a bifunctional compound containing amine, alcohol, mercaptan or phenol groups, at least one of the bifunctional compounds containing a tetraalkyl piperidine radical. The compounds are valuable light stabilizers for synthetic polymers, particularly polyolefin in the form of fibers or films.

The bifunctional compound has the formula HX—R$_1$—Y—H, wherein X represents —O—, —S—,

with R$_3$ being hydrogen, a straight or branched chain alkyl having 1 to 18 C atoms, a cycloalkyl having 5 to 18 C atoms, a substituted or non-substituted aryl having 6 to 18 C atoms, an aralkyl having 7 to 18 C atoms, or R$_3$ represents a piperidine radical of the formula:

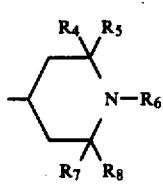

wherein each of R$_4$, R$_5$, R$_7$ and R$_8$, the same or different, are a C1 to C6 alkyl, and R$_6$ is hydrogen, O, a C1 to C18 straight or branched chain alkyl, a C2 to C18 alkenyl or alkynyl, or a C7 to C18 aralkyl;

R$_1$ is a C2 to C18 straight or branched chain alkylene, a C5 to C18 cycloalkylene, a C6 to C18 arylene, and a C7 to C18 aralkylene.

Representatives of such compounds include 2,5-dimethylpiperazine, homopiperazine, 1,2-bis-(2,2,6,6-tetramethyl-4-piperidylamino)-ethane, 1,3-bis-(2,2,6,6-tetramethyl-4-piperidylamino)-propane, 1,6-bis-(2,2,6,6-tetramethyl-4-piperidylamino)-hexane.

These compounds are not however said by Cassandrini et al to be stabilizers; they are only intermediates in the preparation of Cassandrini et al's triazines, which are said to be stabilizers.

Rody and Rasberger, U.S. Pat. Nos. 4,232,131, patented Nov. 4, 1980, 4,233,410, patented Nov. 11, 1980; 4,233,412, patented Nov. 11, 1980; 4,234,699, patented Nov. 18, 1980; 4,234,700, patented Nov. 18, 1980; 4,260,689, patented Apr. 7, 1981; 4,260,691, patented Apr. 7, 1981 and 4,299,926, patented Nov. 10, 1981 provide polymeric compounds which can be used as light stabilizers for plastics and which are condensation polymers and addition polymers which contain a sterically hindered polyalkylpiperidine radical. The recurrent molecular unit contains a polyalkylpiperidine radical of the formula

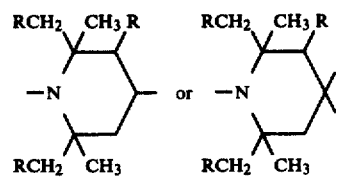

or is substituted by a polyalkylpiperidine side group of the formula

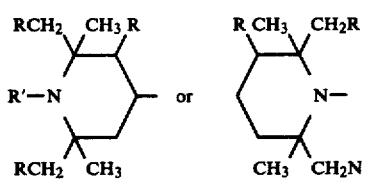

in which R denotes hydrogen or alkyl with 1-5 C atoms and R' denotes hydrogen, alkyl with 1-12 C atoms, alkenyl with 3-8 C atoms, alkynyl with 3-6 C atoms, aralkyl with 7-12 C atoms, alkanoyl with 1-8 C atoms or alkenoyl with 3-5 C atoms, and to copolymers with one another or with polyalkylpiperidine free components.

Examples of such polymers are polyesters, polyethers, polyamides, polyamines, polyurethanes, polyureas, polysulphides, polysulphones, polyimides, polysulphonates, polyphosphates, polyphosphonates, polysilyl esters, polysiloxanes, polyhydrazides, polyhydrazones or polybenzimidazoles.

German Offenlegungsschrift No. 2,719,131 describes condensation and addition polymers, the recurring structural unit of which contains a polyalkylpiperidine residue of the formula

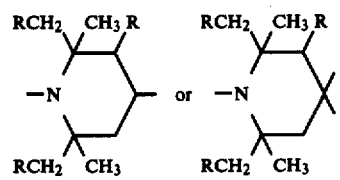

or is substituted by a polyalkylpiperidine side group of the formula

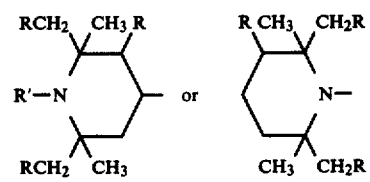

in which R is hydrogen or alkyl having 1-5 C atoms and R' is hydrogen, alkyl having 1-12 C atoms, alkenyl having 3-8 C atoms, alkynyl having 3-6 C atoms, aralkyl having 7-12 C atoms, alkanoyl having 1-8 C atoms or alkenoyl having 3-5 C atoms, and also copolymers thereof with one another or with polyalkylpiperidine-free components, which polymers and copolymers can be used as light stabilizers for plastics.

Preferably, the polymers are polyesters, polyamides, polyurethanes, polyureas, polysilyl esters, polyethers, polyamines, polycarbonates and their copolymers, in which the recurring unit in the molecule contains a polyalkylpiperidine residue, and especially those polymers which can be represented by the general formulae I–VII

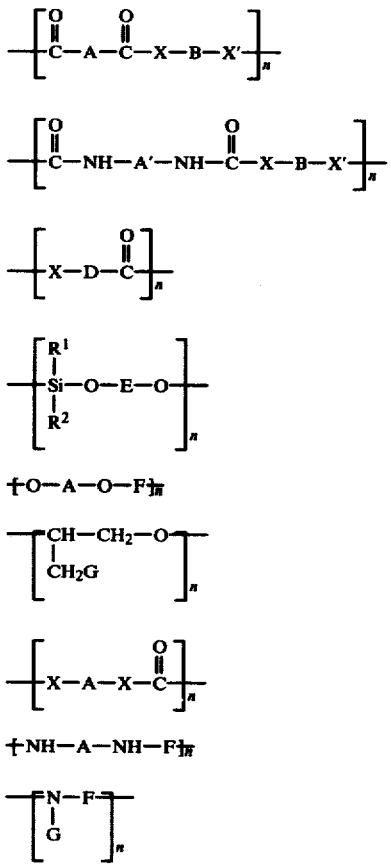

in which X and X' are oxygen or NY, Y is hydrogen, alkyl, cycloalkyl, aralkyl, aryl or a polyalkylpiperidine radical, $R_1$ and $R_2$ are methyl, ethyl or phenyl, A, A', B, B', D, E and F are divalent organic radicals and G is a monovalent organic radical, at least one of the radicals Y, A, A', B, B', D, E, F and G containing a polyalkylpiperidine residue in each of the formulae I to VII. The index n has a value of 2–50, so that the polymers are those of relatively low molecular weight. If these polymers are linear, they carry end groups which in the main correspond to the functional groups of the starting materials used for their preparation. For example, polyesters which are prepared from diols and dicarboxylic acids have hydroxyl and carboxyl end groups. Depending on the molar ratio of the components used, the end groups in these polyesters can be mainly hydroxyl groups or mainly carboxyl groups, or the two types of end groups are present in about the same numbers. Other types of end groups which can be present in the polymers of the formulae I to VII are amino groups, lower alkyl-carboxylate groups, halogen groups, isocyanate groups or epoxy groups. Such end groups can have an adverse effect when the polymers are used as light stabilizers in plastics, in particular when the degree of polymerization n is low and the proportion of end groups is thus relatively high. During the shaping processing of the plastics stabilized with these polymeric light stabilizers, temperatures can arise at which the end groups are no longer stable. An undesired reaction with the plastic can also occur or a partial decomposition of the polymeric light stabilizer can take place. As a result of this, discolorations can arise, the light stabilizing action can be reduced or the properties of the plastics can be changed.

Rody and Nikles, U.S. Pat. No. 4,234,707, patented Nov. 18, 1980, overcomes the adverse effects of such end groups by blocking the end groups, during or after the preparation of the polymers, by the addition of compounds which react monofunctionally with the end groups. For example, in the case of a polyester which carries both hydroxyl and carboxyl groups, the hydroxyl groups can be blocked by allowing the polyester to react, after it has been prepared, with a monocarboxylic acid or a functional derivative thereof, (for example the acid chloride or acid anhydride), or by adding a small amount of a monocarboxylic acid or a derivative thereof during the preparation of the polyester from a dicarboxylic acid and a diol. Analogously, amino groups can also be blocked by monocarboxylic acids or functional derivatives thereof.

Hydroxyl groups and amino groups can also be blocked by monochlorotriazines, by monoepoxides or by monoisocyanates. Isocyanate end groups and epoxide end groups can be blocked by monoalcohols or by primary or secondary monoamines. Halogen end groups can be blocked by monoamines, by alkali metal alkoxides or by trialkyl phosphites.

Cyclic anhydrides of dicarboxylic acids can also react monofunctionally towards primary amino groups by forming a cyclic imide group.

Soma, Morimura, Yoshioka and Kurumada, U.S. Pat. No. 4,265,803, patented May 5, 1981, provides polymers containing sterically hindered polyalkylpiperidines which are useful as stabilizers for synthetic polymers.

The polymers have groups containing polyalkylpiperidines represented by the general formulae:

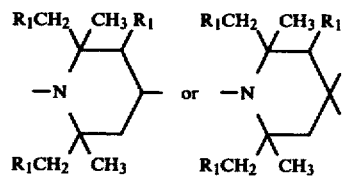

(wherein, $R_1$ represents hydrogen atom or methyl group) linked in the main chain via bridging members containing groups having the formula

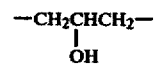

The polymers show superior stabilizing effect for various polymeric materials against light- and heat degradation thereof, with less vaporization and exudation therefrom.

The polymers of the invention containing polyalkylpiperidines are represented by the following formula (I):

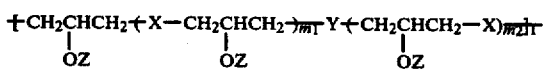

In the above formula, 1 represents an integer of from 2 to 50, preferably 2–10, most preferably 2–6.

Both $m_1$ and $m_2$ represent 0, or one of them represents 1 and another represents 0.

X represents a group of formula

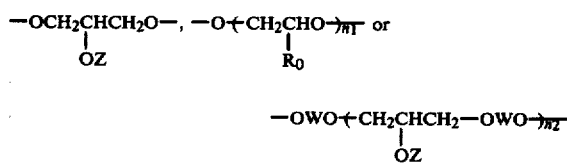

$R_0$ represents hydrogen atom or methyl group, preferably hydrogen atom.

$n_1$ represents an integer of from 1 to 10, preferably 1.
$n_2$ represents 0 or an integer of from 1 to 10, preferably 0.

In accordance with this invention, poly-(2,2,6,6-tetramethylpiperidyl amino) alkanes are provided having the formula (I) or (II):

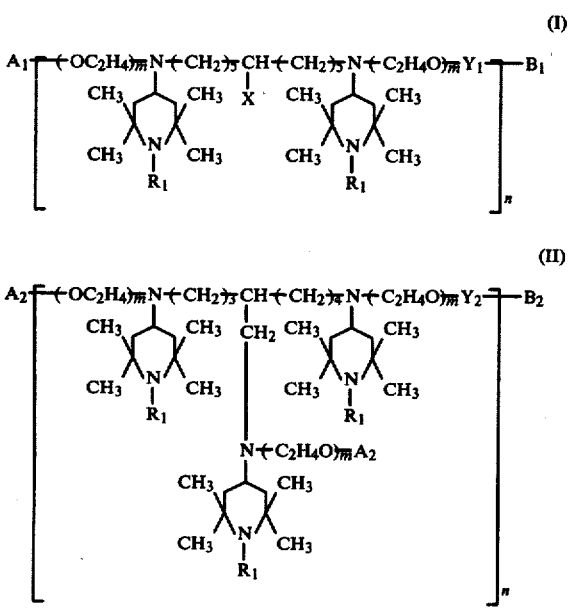

The compounds of Formula I are undecylene-1,11-diamine derivatives having piperidylamino substitutents on each nitrogen atom or undecylene 1,6,11-triamine derivatives having piperidylamino substituents on each nitrogen atom, and polymers thereof optionally including oxyethylene groups in the polymer chain.

The compounds of Formula II are nonylene-1,4-9-triamine derivatives having piperidylamino substituents on each nitrogen atom, and polymers thereof optionally including oxyethylene units in the polymer chain.

In the above Formulae I and II:

X is hydrogen or

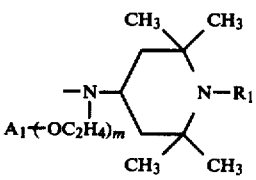

$Y_1$ is carbonyl

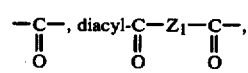

where $Z_1$ is a single bond; saturated or unsaturated alkylene having from one to twelve carbon atoms, or phenylene; dicarbamoyl

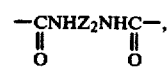

where $Z_2$ is alkylene having from two to twelve carbon atoms; cyclohexylene and alkylcyclohexylene having five to ten carbon atoms; or phenylene and alkyl phenylene having six to twelve carbon atoms; diphenylene; diphenylene ether; diphenylene alkane, the alkane having one to four carbon atoms; or

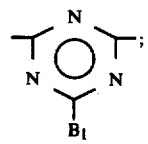

$A_1$ is hydrogen, alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or $B_1$—$Y_1$—;

$B_1$ is —$OR_2$,

or

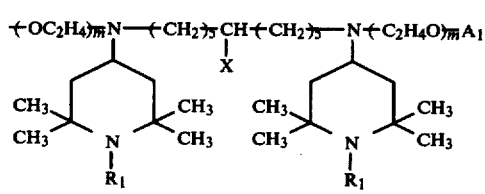

$Y_2$ is carbonyl

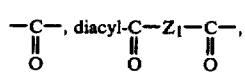

where $Z_1$ is a single bond; saturated or unsaturated alkylene having from one to twelve carbon atoms; or phenylene; dicarbamoyl

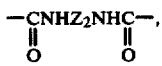

where $Z_2$ is alkylene having from two to twelve carbon atoms; cyclohexylene and alkylcyclohexylene having five to ten carbon atoms; or phenylene and alkyl phenylene having six to twelve carbon atoms; diphenylene; diphenylene ether; diphenylene alkane, the alkane having one to four carbon atoms; or

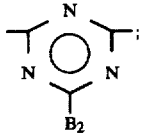

$A_2$ is hydrogen, alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or $B_2-Y_2-$;

$B_2$ is $-OR_2-$,

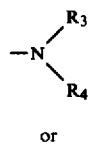

or

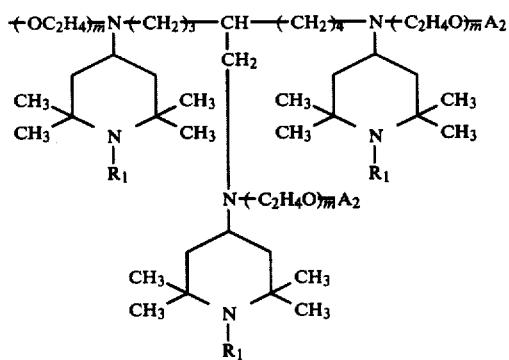

$R_1$ is hydrogen, alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or oxy;

$R_2$ is alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or aryl;

$R_3$ and $R_4$ each is hydrogen, alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or

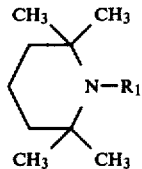

m is 0 to 10;

n is 1 to 20.

When n is 1, $-Y_1-B_1$ and $-Y_2-B_2$ each may be acryloyl; phenoyl, alkylphenoyl, hydroxyphenoyl and alkylhydroxyphenoyl having from six to ten carbon atoms.

The compounds of Formula (I) where X is

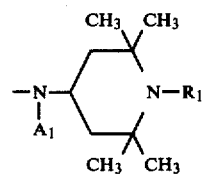

and the compounds of Formula (II) are preferred because of their high stabilizing effectiveness.

Exemplary $A_1$, $A_2$, $R_1$, $R_2$, $R_3$ and $R_4$ alkyl are methyl, ethyl, propyl, isopropyl, butyl, amyl, hexyl, heptyl, octyl, 2-ethylhexyl, nonyl, decyl, isodecyl, dodecyl, octadecyl; exemplary phenalkyl are benzyl and phenmethyl, phenmethyl and phenylethyl; exemplary hydroxyalkyl are 2-hydroxyethyl, 2-hydroxypropyl and 2-hydroxybutyl, hydroxyamyl, hydroxyhexyl, hydroxylauryl, hydroxystearyl; and exemplary epoxyalkyl are 2,3-epoxypropyl, 2,3-epoxybutyl; 1,2-epoxybutyl, epoxyamyl, epoxyhexyl, epoxystearyl.

Exemplary acyl as $A_1$, $A_2$, $R_1$ and $-Y_1-B_1$ and $-Y_2-B_2$ (when n=1) are acetyl, propionyl, butyroyl, octanoyl, lauroyl, stearoyl; exemplary phenoyl, hydroxyphenoyl, alkylphenoyl and alkylhydroxyphenoyl are benzoyl, salicyloyl, 3,5-di-t-butyl-4-hydroxybenzoyl and 3,5-di-t-butyl-4-hydroxy phenylpropionyl.

Exemplary $R_2$ aryl are phenyl, naphthyl, tolyl, xylyl, t-butylphenyl, 2,4-di-t-butylphenyl and nonylphenyl.

Exemplary $Y_1$ and $Y_2$ diacyl are derived from the following dicarboxylic acids; oxalic acid, malonic acid, succinic acid, glutaric acid, adipic acid, azelaic acid, sebacic acid, dodecanedioic acid, maleic acid, phthalic acid, isophthalic acid and terephthalic acid.

Exemplary $Y_1$ and $Y_2$ dicarbamoyl are derived from the following diisocyanates: hexamethylenediisocyanate, lysine diisocyanate, isophoronediisocyanate, phenyldiisocyanate, tolylenediisocyanate, diphenyletherdiisocyanate, diphenyl methanediisocyanate, xylylenediisocyanate, bis(isocyanato methyl)cyclohexane and 3-(2'-isocyanatocyclohexyl) propyl isocyanate.

Examples of the compounds of Formula (I) and (II) are shown below:

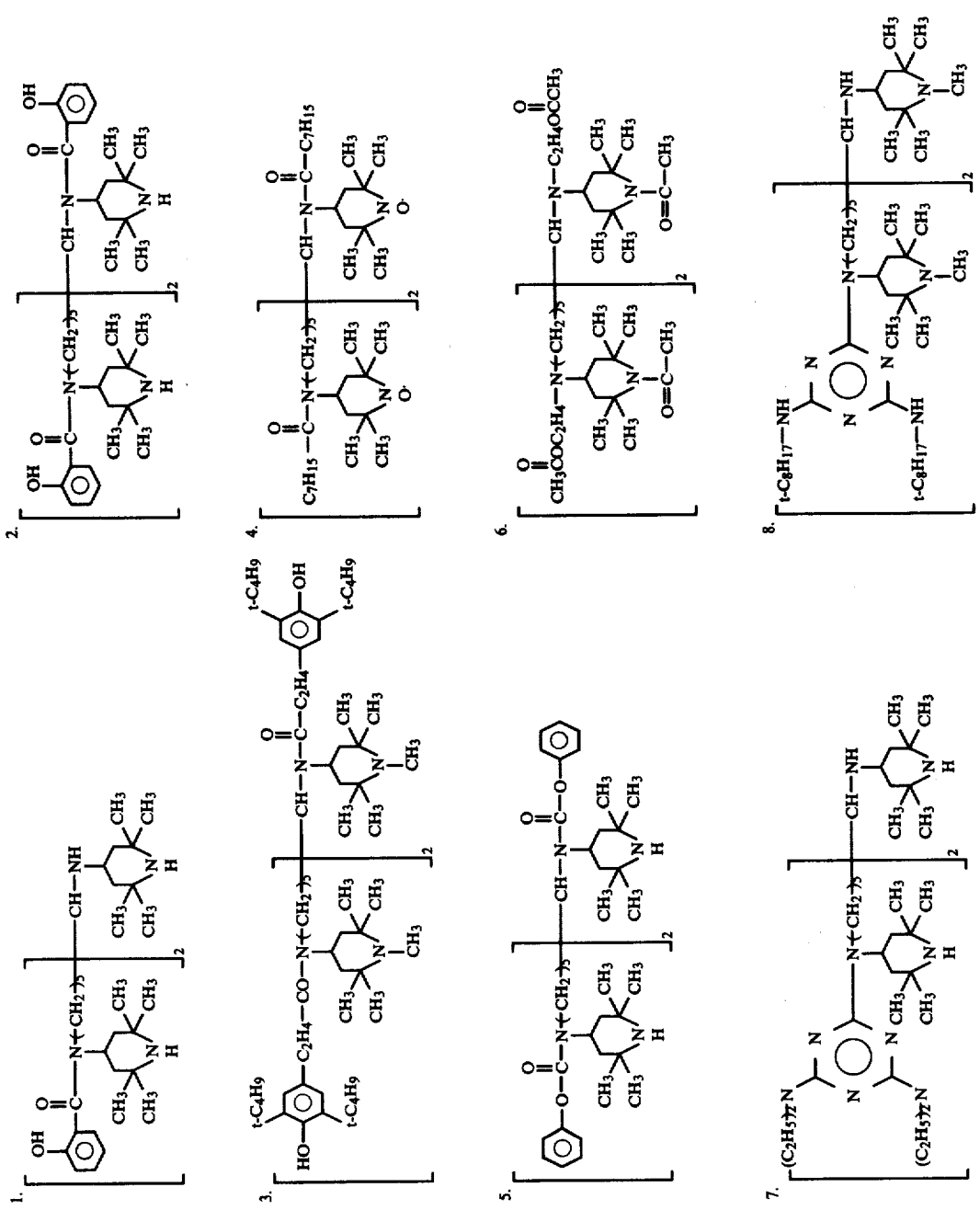

-continued
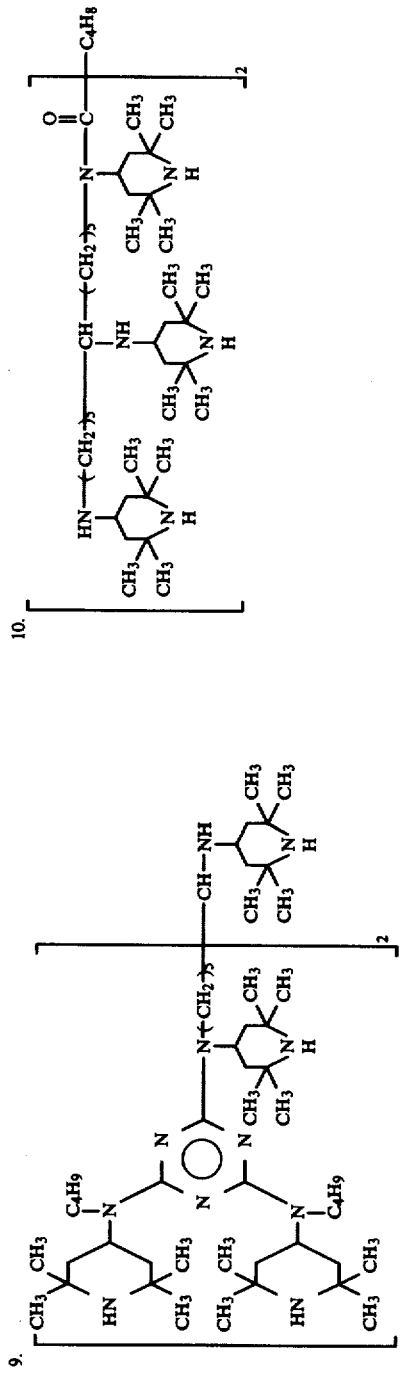
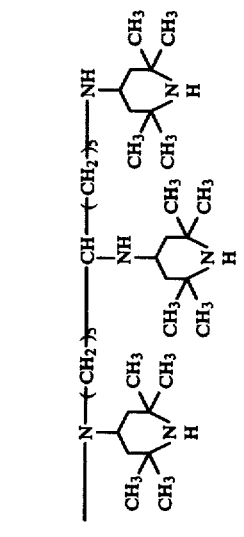
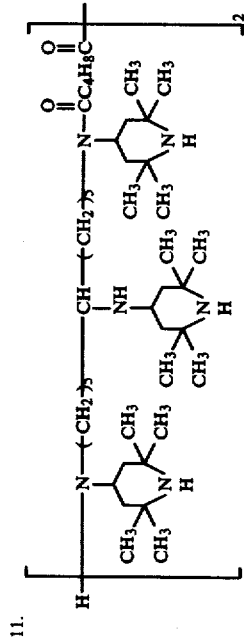
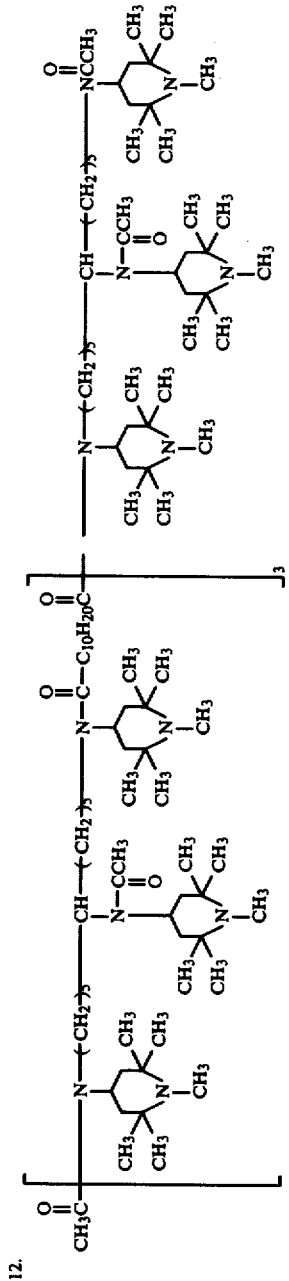

-continued
13.
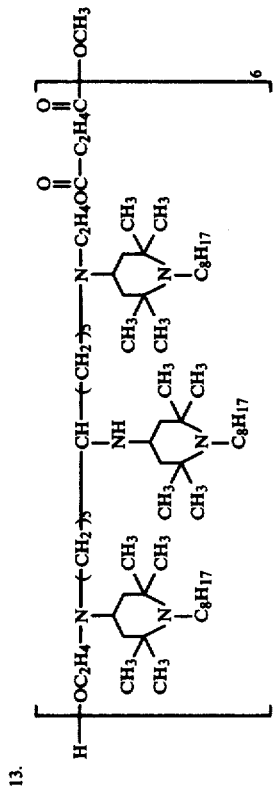
14.
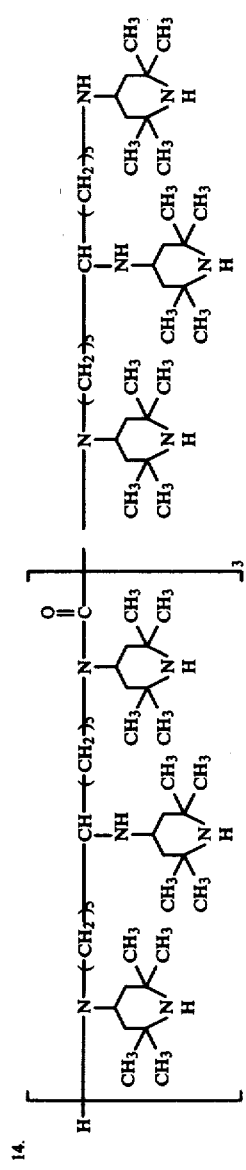
15.
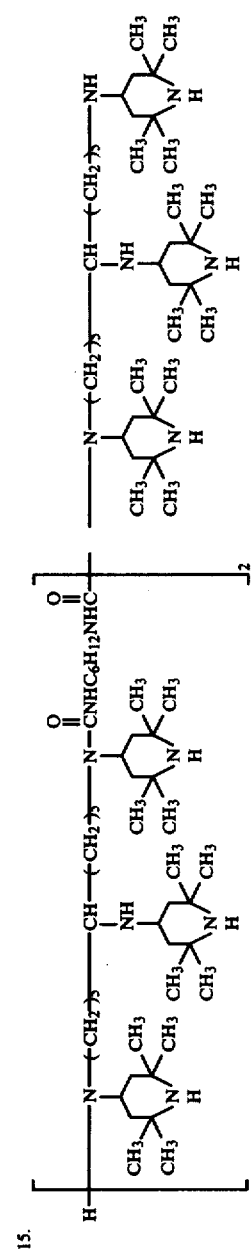

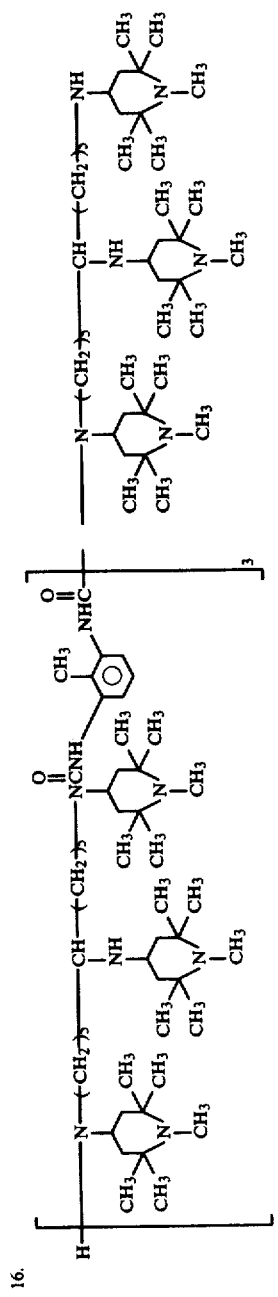
16.
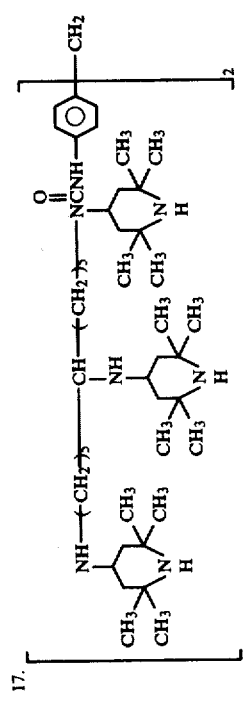
17.
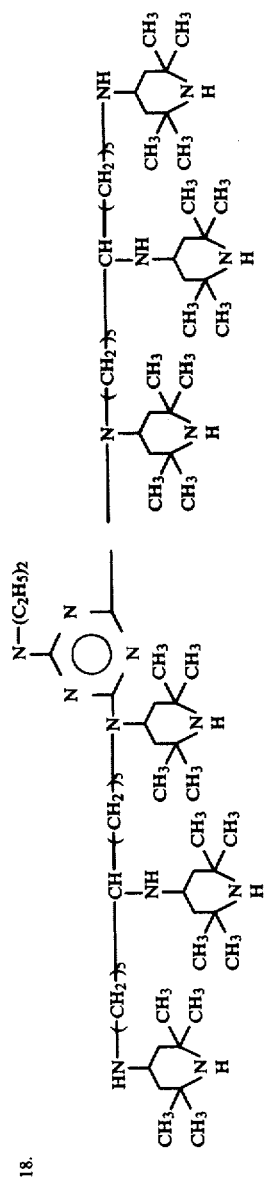
18.

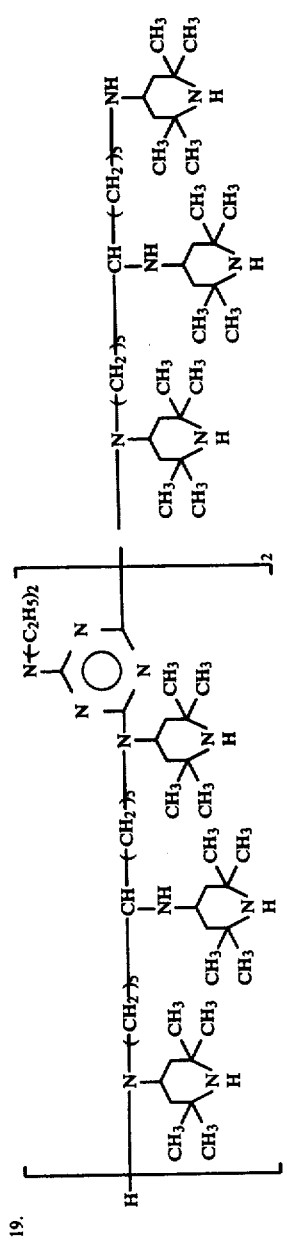
19.
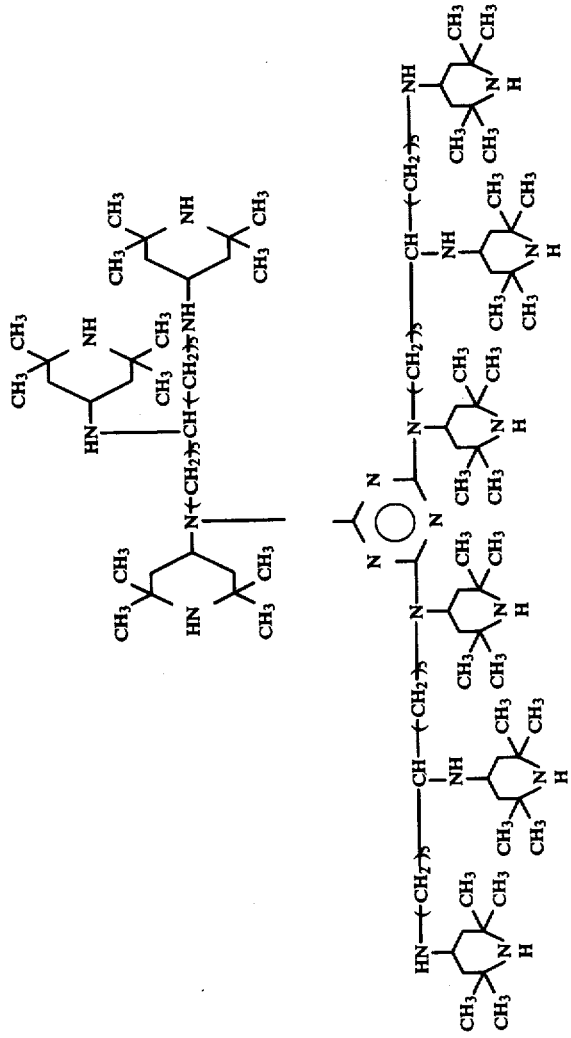
20.

21.
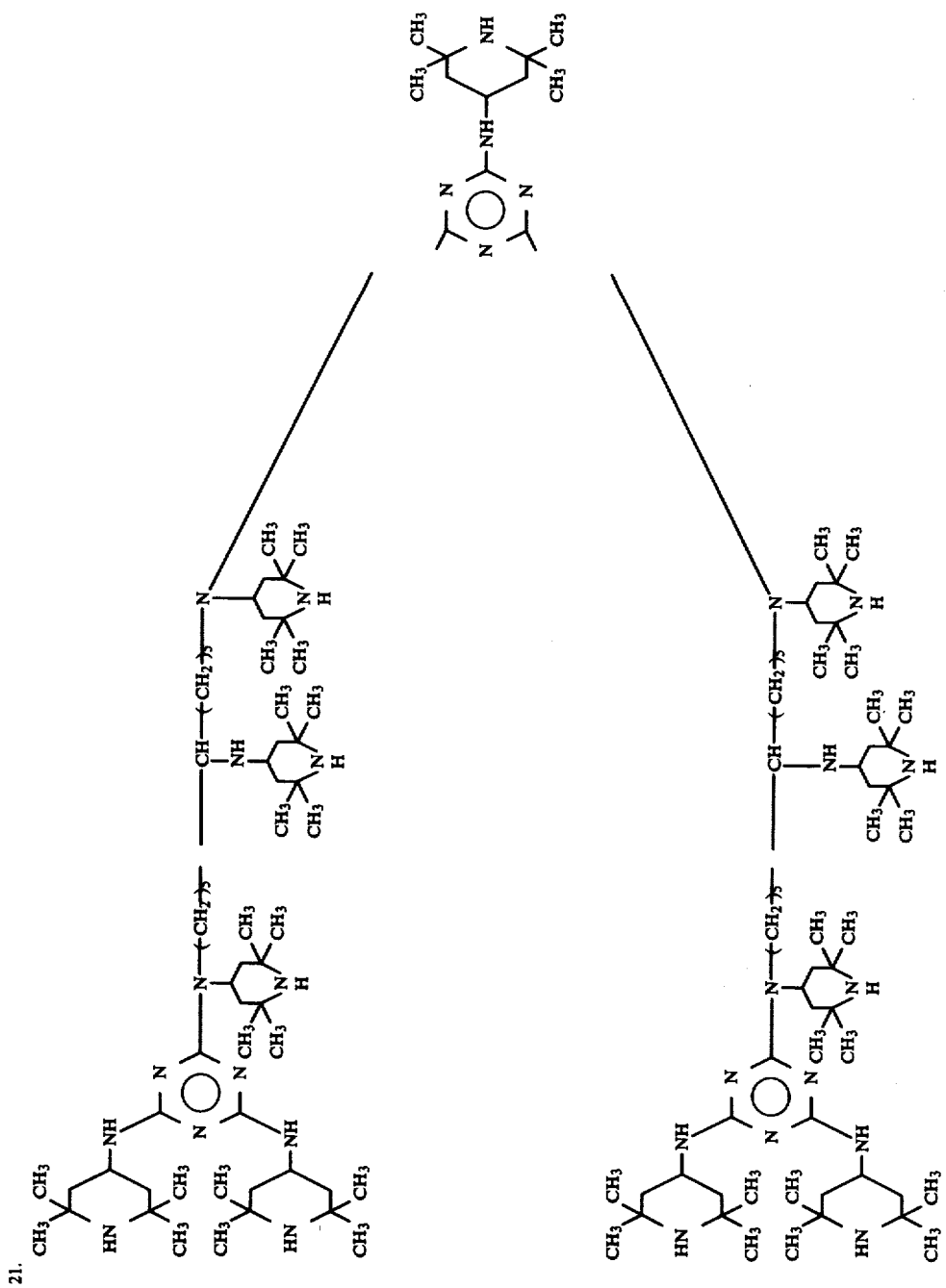

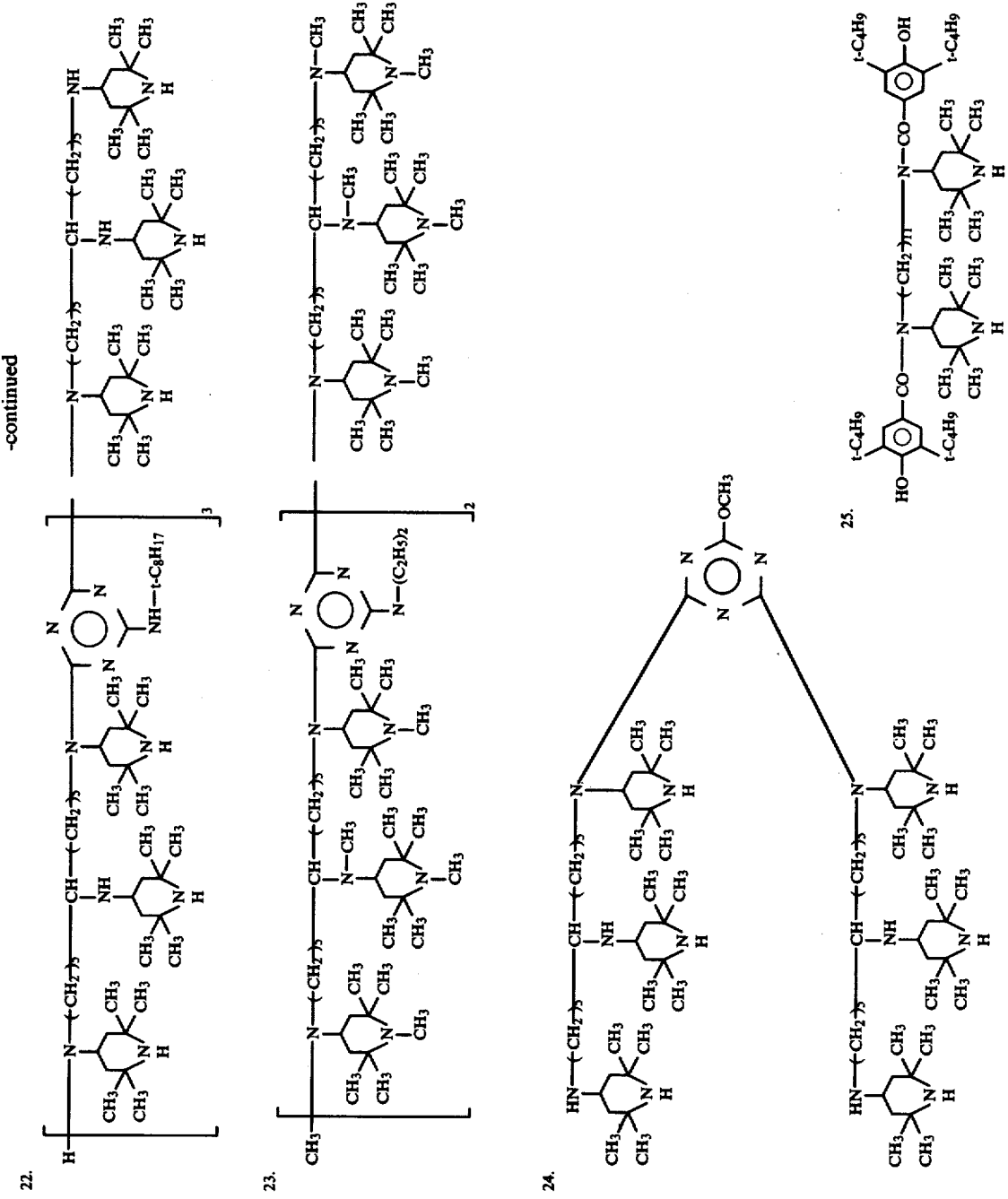

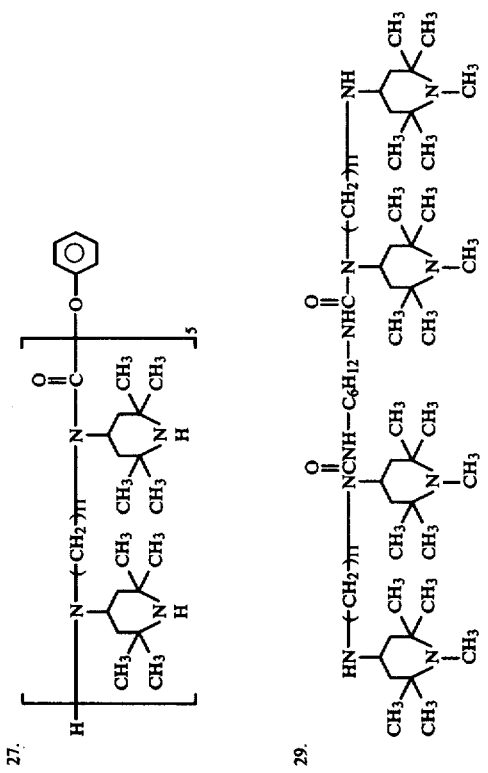
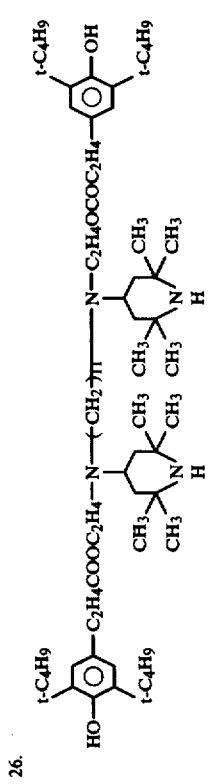
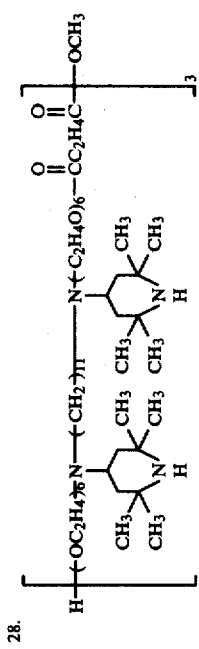
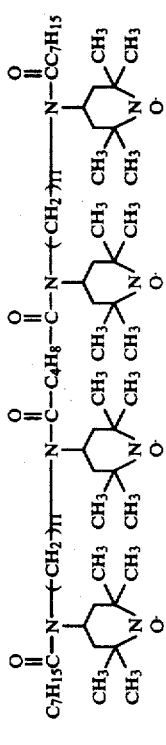
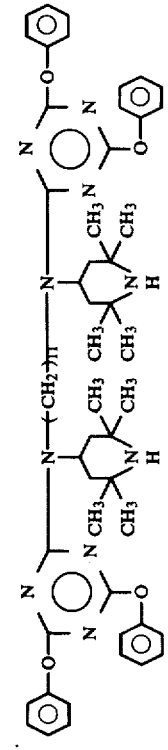
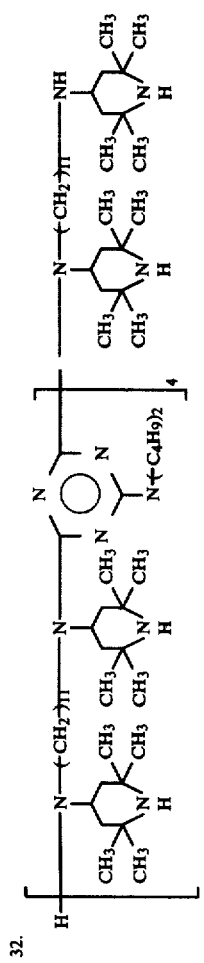

-continued
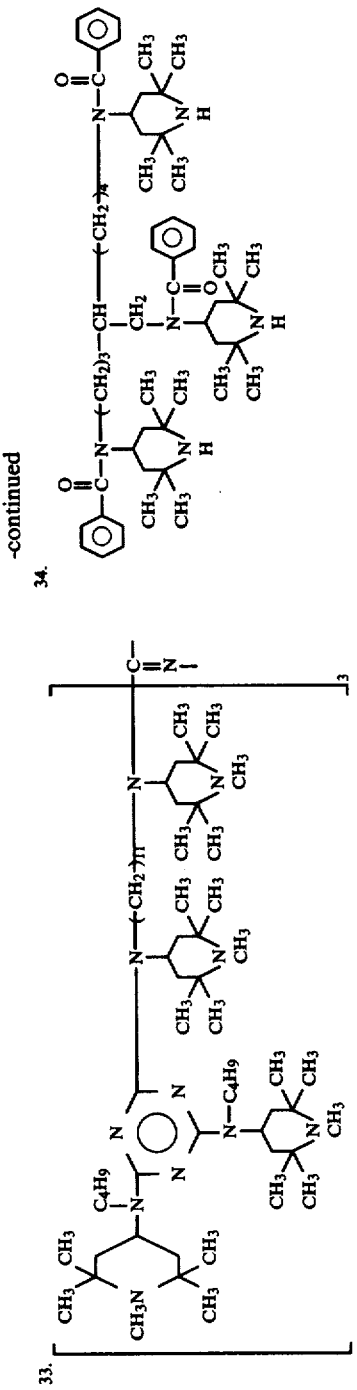
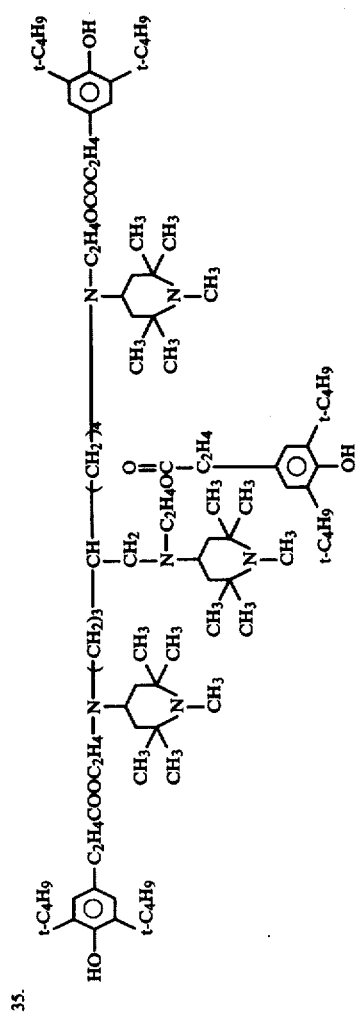
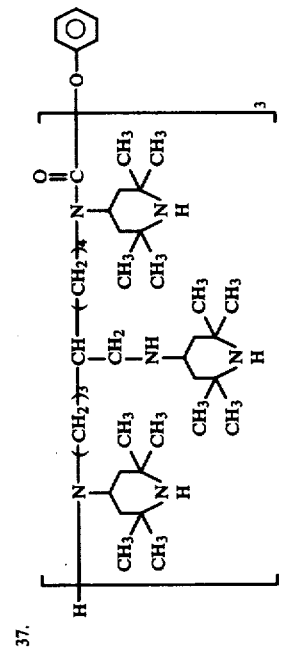

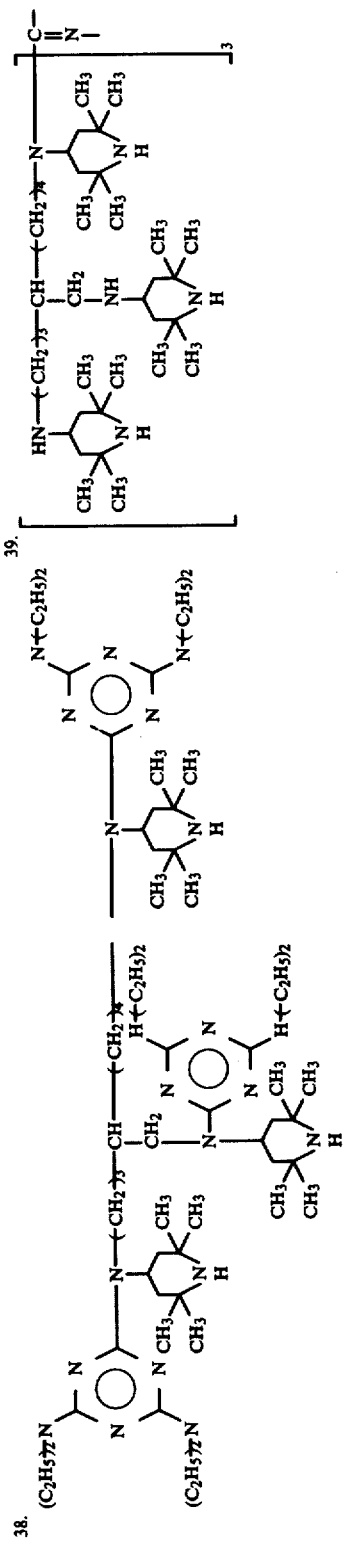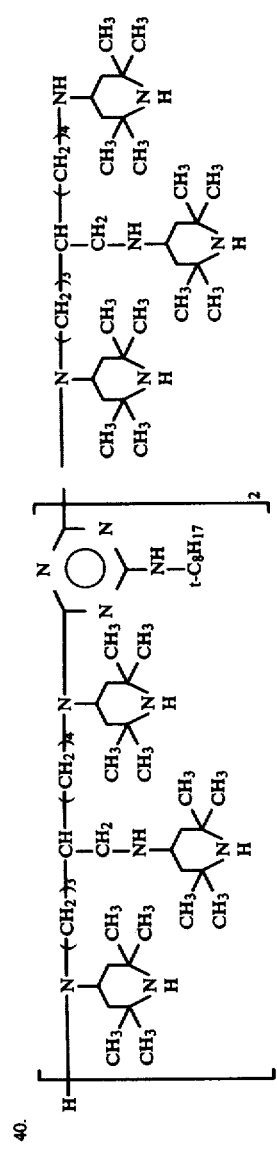

-continued
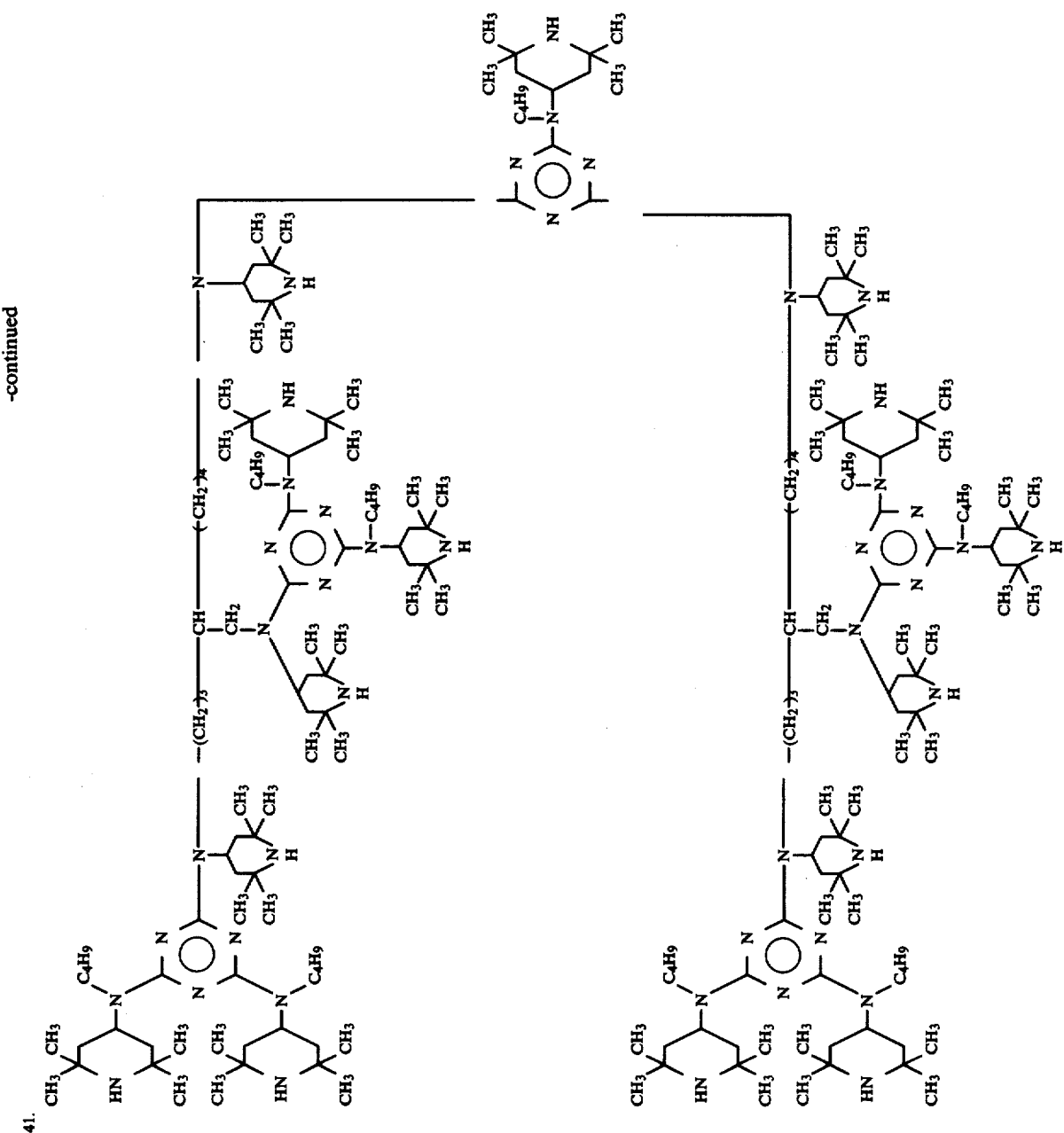
41.

The compounds of formulae (I) and (II) can be prepared easily by the reaction of the corresponding bis- or tris-(tetramethyl piperidinylamino) undecanes or tris-(tetramethyl piperidinylamino) nonanes with the corresponding carboxylic acid or ester, anhydride or acid chloride thereof, carbonic acid diester, diisocyanate, cyanuric halide or mono- or di-substituted cyanuric halide. The following Examples illustrate preferred embodiments of preparation of the compounds listed above.

EXAMPLE I

Preparation of

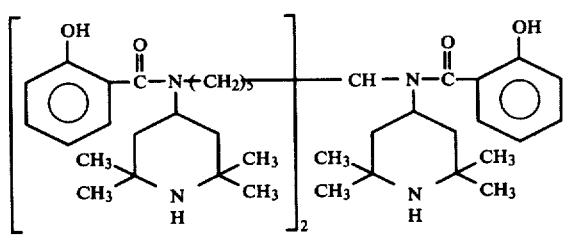

1,6,11-Tris(2,2,6,6-tetramethyl-4-piperidinylamino) undecane 5.0 g, phenyl salicylate 5.5 g and potassium carbonate 31.5 mg were heated and stirred at from 120° to 145° C. for 6 hours while removing the phenol produced under reduced pressure. Then, 100 ml of toluene was added and the reaction mixture passed through a bed of absorbent. After filtration, n-hexane was added to the filtrate, and pale yellow powder that precipitated was filtered off. m.p. 78–84° C.

| | Elemental analysis | | |
|---|---|---|---|
| | C % | H % | N % |
| Found | 72.48 | 9.32 | 8.70 |
| Calcd. (as $C_{59}H_{90}N_6O_6$) | 72.39 | 9.20 | 8.59 |

EXAMPLE II

Preparation of

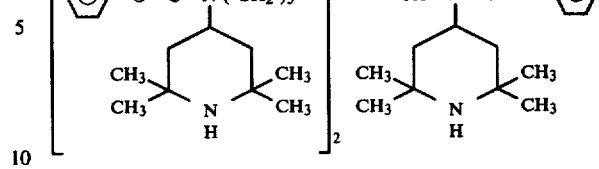

1,6,11-Tris(2,2,6,6-tetramethyl-4-piperidine amino) undecane 5.0 g, diphenyl carbonate 5.5 g, potassium carbonate 60 mg and xylene 5 ml were heated and stirred at from 100° to 145° C. for 7 hours, while removing the phenol produced under reduced pressure.

Then, 100 ml of toluene was added and the reaction mixture passed through a bed of absorbent. The solvent from the filtrate was evaporated, and a pale brown semi solid was obtained.

Infrared spectral analysis showed strong absorption at 1710 cm$^{-1}$, corresponding to the urethane bond.

| Elemental analysis: | | | |
|---|---|---|---|
| | C % | H % | N % |
| Found | 72.41 | 9.24 | 8.64 |
| Calcd. (as $C_{59}H_{90}N_6O_6$) | 72.39 | 9.20 | 8.59 |

EXAMPLE III

Preparation of

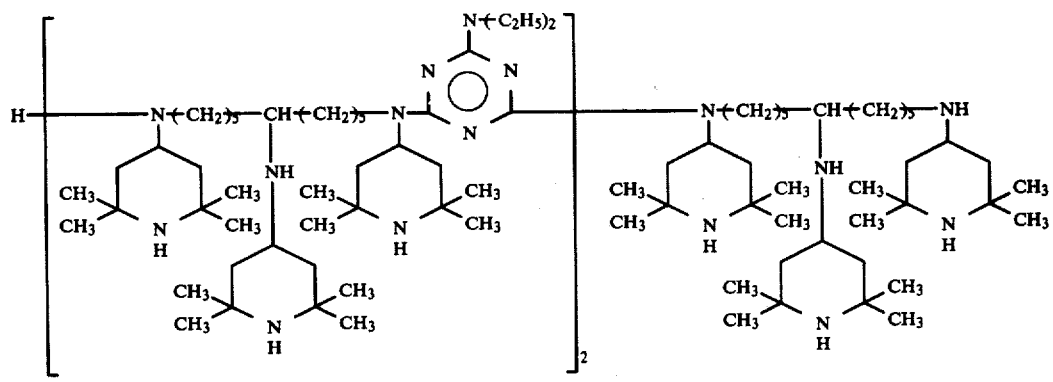

1.6,11-Tris(2,2,6,6-tetramethyl-4-piperidinylamino)undecane 1.9 g, 2-diethylamino-4,6-dichlorotriazine 0.44 g, xylene 5 ml and powdered sodium hydroxide 0.3 g were heated and stirred at from 100° to 165° C. for 6 hours.

Then, 50 ml of toluene was added, and the solution washed with water and dried, followed by filtration through Celite. The solvent from the filtrate was evaporated, and a white powder obtained.

m.p. 60°–70° C., M.W.=2300–2400

Small amounts of the poly(piperidyl amine)alkane of this invention when combined with synthetic resin improve the light stability of the resin. The amount of the poly(piperidyl amine)alkane is generally within the range from about 0.001 to about 10 parts by weight, preferably from about 0.1 to about 3 parts by weight, per 100 parts by weight of resin.

Synthetic resins that can have their resistance to deterioration enhanced with poly(piperidyl amine)alkanes according to this invention include α-olefin polymers such as polyethylene, polypropylene, polybutene, poly-3-methylbutene, or mixtures thereof, and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The poly(piperidyl amine)alkane of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$X_1$ and $X_2$ are integers from one to four, and the sum of $x_1$ and $x_2$ does not exceed six.

The polycyclic phenol phenol is one having at least two aromatic nuclei linked by a polyvalent linking radical, as defined by the formula:

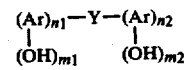

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar-Y-Ar-Y-Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

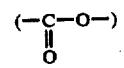

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

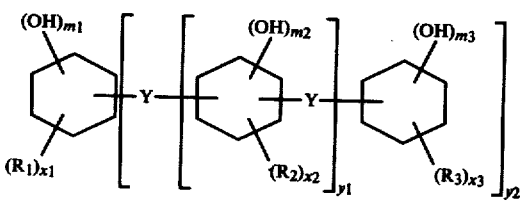

wherein

R₁, R₂ and R₃ are inert substituent groups as described in the previous paragraph;

m₂ and m₃ are integers from one to a maximum of five;

m₂ is an integer from one to a maximum of four;

x₁ and x₃ are integers from zero to four, and x₂ is an integer from zero to three;

y₁ is an integer from zero to about six and y₂ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

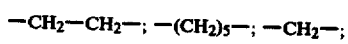

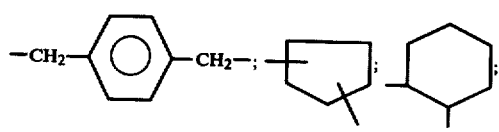

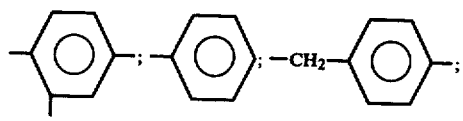

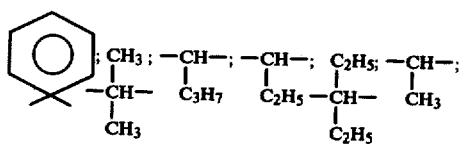

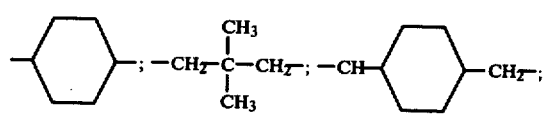

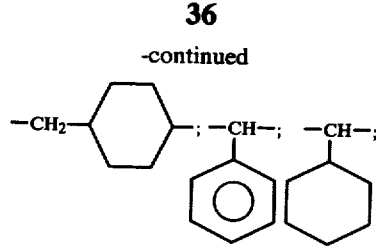

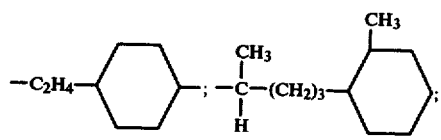

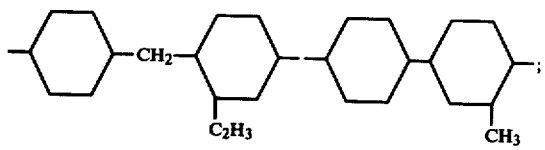

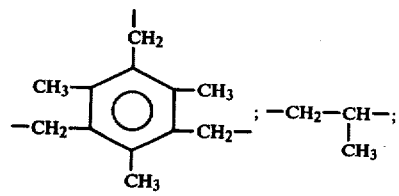

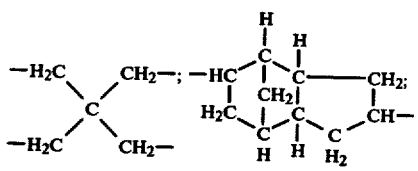

(2) Y groups where only atoms other than carbon link the aromatic rings, such as —O—, —S—,

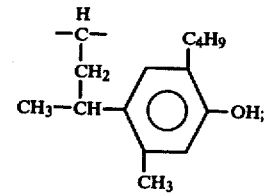

and —(S)ₓ— where x is a number from one to ten;

(3) Y groups made up of more than a single atom including both carbon and other atoms linking the aromatic nuclei, such as:

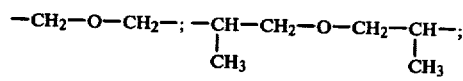

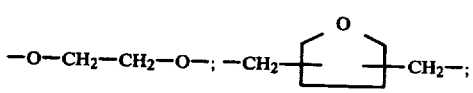

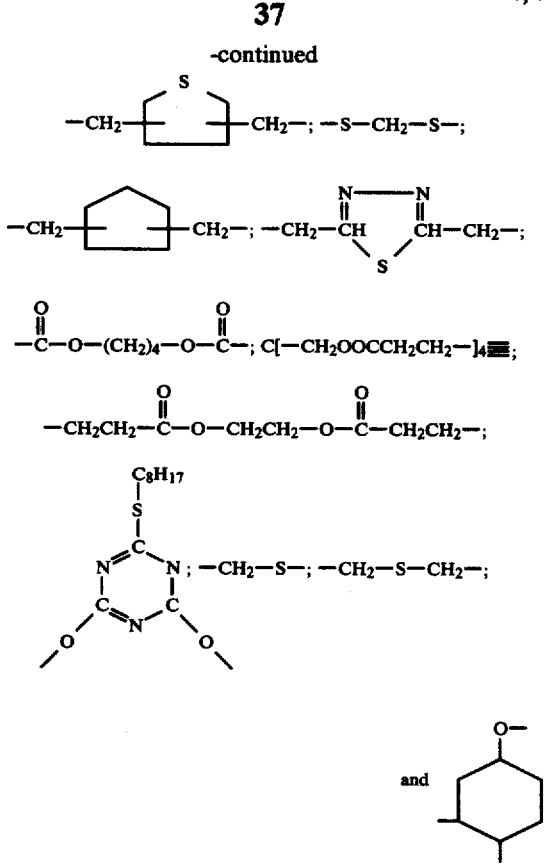

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxycresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis (2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiarybutyl-5'-methyl-benzyl)-4-methylphenol, 4,4'-bis-(2-tertiarybutyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis (naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxyphenyl)-(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonyl-phenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxyl-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid] glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3(3,5-di-t-butyl-4-hydroxyphenyl)propionate] methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

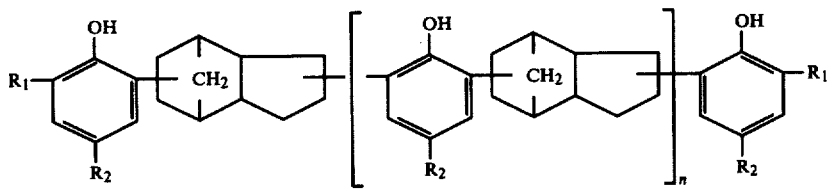

in which

R₁ and R₂ are lower alkyl, and can be the same or different, and n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

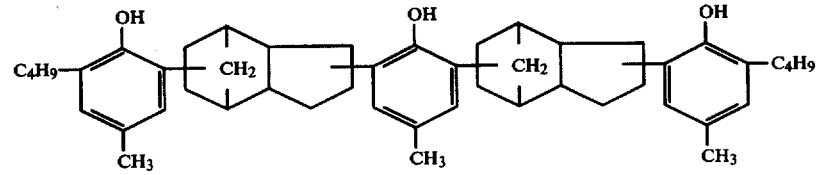

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkylsubstituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

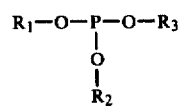

in which

R₁, R₂ and R₃ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

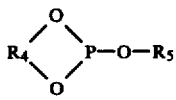

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

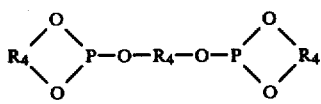

More complex triphosphites are formed from trivalent organic radicals, of the type:

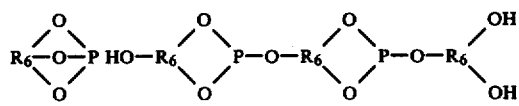

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

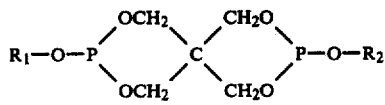

where $R_1$ and $R_2$ are selected from the group consisting of aryl, alkyl, aryloxyethyl, alkyloxyethyl, aryloxyethoxyethyl, alkyloxyethoxyethyl and alyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

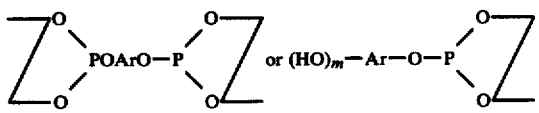

in which

Ar is a mono or bicyclic aromatic nucleus and m is an integer of from 0 to about 5.

is one or a plurality of organic radicals as defined above for $R_1$ to $R_6$, taken singly or together in sufficient number to satisfy the valences of the two phosphite oxygen atoms.

One or both

radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl) phosphite, tri-(t-nonylphenyl)phosphite, benzyl methyl isopropyl phosphite, butyl dicresyl phosphite, isooctyl di(octylphenyl) phosphite, di(2-ethylhexyl)(isooctylphenyl)phosphite, tri (2-cyclohexylphenyl)phosphite, tri-α-naphthyl phosphite, tri (phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(- lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di-(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy)ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-thio-bis(2-tertiary-butyl-5-methylphenol))di-phenyl phosphite, tri-(4,4'-n-butylidene-bis(2-tertiary-butyl-5-methylphenol))phosphite, (4,4'-benzylidene-bis(2-tertiary-butyl-5-methyl-phenol)-)diphenyl phosphite, isooctyl 2,2'-bis(-parahydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl-(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bisphenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))-phosphite, (4,4'-thio-bis(2-tertiary-butyl-5-methylphenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)propane)phospite, mono(4,4'-butylidene-bis(2-tertiary-butyl-5-methylphenol)phosphite, bis(4,4'-thio-bis(2-tertiary-butyl-5-methylphenol))phosphite, mono-2-ethylhexyl-mono-2,2'-methylene-bis(4-methyl-6,1'-methyl-cyclohexyl)phenol phosphite, bis(2,2'-bis(para-hydroxyphenyl)propane)phosphite, monoisooctylmono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, triisooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

$$R_1OOCCH_2CH_2-S-CH_2CH_2COOY$$

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$$-XO[OCCH_2CH_2SCH_2CH_2COOXO]_nOCCH_2CH_2-S-CH_2CH_2COOZ$$

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
(a) $R_1OOCCH_2CH_2SCH_2CH_2COOH$ (b) R₁OOCCH₂CH₂SCH₂CH₂COOR₂
(c) R₁O[OCCH₂CH₂SCH₂CH₂COOX—O]-ₙOCCH₂CH₂SCH₂CH₂COOZ
(d) R₁OOCCH₂CH₂SCH₂CH₂COOM In the above formulae R₁ and R₂, M, X and Z are the same as before and the vaklue of n₁ can range upwards from 1, but there is no upper limit on n₁ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, R₂ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

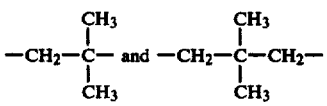

arylene radicals such as phenylene

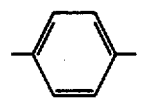

methylenephenylene

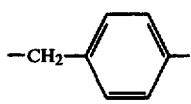

dimethylene phenylene

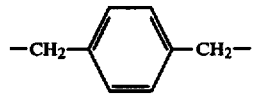

and alicyclylene such as cyclohexylene

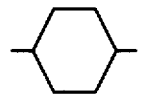

and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

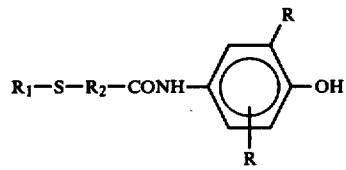

R is alkyl of one to eight carbon atoms, R₁ is alkyl of six to twenty-four carbon atoms, and R₂ is alkylene of one to six carbon atoms.

(2) Thioalkanoic acid amides of 1,3,5-triazines of Ozeki et al Japanese Pat. No. 20,366/68 having the formula:

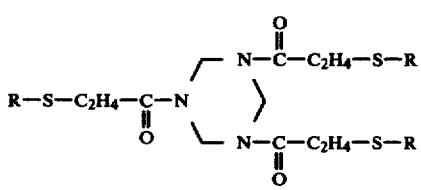

R is alkyl of eight to eighteen carbon atoms.

(3) Bis-thioalkanoic acid amides of Yamamoto et al Japanese Pat. No. 23,765/68 having the formula:

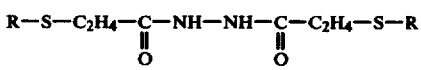

R is alkyl of more than six carbon atoms, aryl or aralkyl.

(4) Bis-thioalkylanoic acid amides of Ozeki et al Japanese Pat. No. 26,184/69 having the formula:

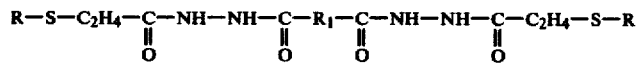

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

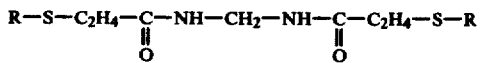

R is alkyl of more than six carbon atoms, aryl, or aralkyl.

(6) Thioalkanoic acid amide derivatives of Minagawa et al, published Japanese application No. 106,484/74 having the formula:

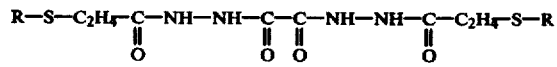

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

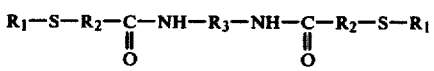

wherein:
$R_1$ is alkyl having from one to about fifty carbon atoms;
$R_2$ is alkylene having from one to about three carbon atoms; and
$R_3$ is alkylene having from about two to about twelve carbon atoms.

β-Alkylthiopropionic acid esters having the general formula:

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl)5-chlorobenzotriazole, 2(2-hydroxy-3,5-di-t-amylphenyl)benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octylphenolate), nickel-monoethyl(3,5-di-t-butyl-4-hydroxybenzyl)phosphonate, substituted acrylonitriles such as methyl-α-cyano-β-methyl-β-(p-methoxy phenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 10% total stabilizers including the poly(piperidyl amine)alkane of the invention by weight of the polymer are satisfactory. Preferably, from 0.01 to 5% is employed for optimum stabilization.

The stabilizer systems of the invention are readily rendered in solid particulate form, comprising a blend of:

(a) poly(piperidyl amine)alkane light stabilizer in an amount of from about 10 to about 35 parts by weight; and optionally:

(b) a phenolic antioxidant in an amount from about 10 to about 35 parts by weight; and/or (c) other heat or light stabilizers in an amount of from about 10 to about 35 parts by weight.

The poly(piperidyl amine) alkane light stabilizer of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples in the opinion of the inventors represent preferred embodiments of synthetic resin compositions containing the poly(piperidylamino)alkane light stabilizers of the invention.

EXAMPLES 1 TO 12

Polypropylene compositions were prepared using stabilizers of the invention and three of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table I | 0.2 |

The compositions were thoroughly blended in a Brabender Plastograph, and then compression-molded to form sheets 0.3 mm thick. Pieces 2.5 cm$^2$ were cut off from the sheets and exposed to a high voltage mercury lamp. The hours to failure were noted, and are shown in Table I.

TABLE I

| Example No. | Stabilizer | Hours to Failure |
|---|---|---|
| Control 1 | Polymer of 2,4-dichloro-6-n-butylamino-1,3,5-triazine with 1,6-bis(2,2,6,6-tetramethyl-4-piperidinylamino) hexane (M.W. = 3,000) | 430 |
| Control 2 | Polyamide of 1,6-bis(2,2,6,6-tetramethyl-4-piperidinylamino) hexane with adipic acid (M.W. = 2,500) | 370 |
| Control 3 | N,N'—Bis(2,2,6,6-tetramethyl-4-piperidinyl)-N,N'—bis($\beta$-3,5-di-t-butyl-4-hydroxyphenylpropionyl oxyethyl)-1,6-hexanediamine | 310 |
| Example 1 | [structure] | 780 |
| Example 2 | [structure] | 750 |
| Example 3 | [structure] | 810 |

TABLE I-continued
| Example No. | Stabilizer | Hours to Failure |
|---|---|---|
| Example 4 | 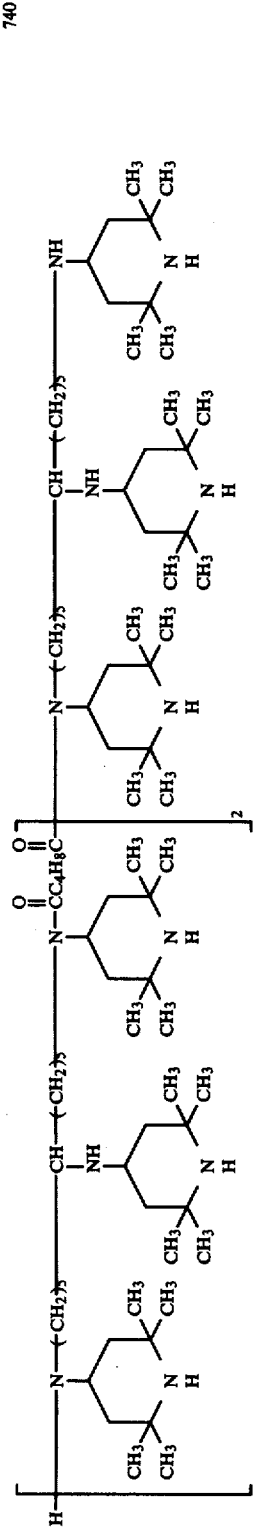 | 740 |
| Example 5 | 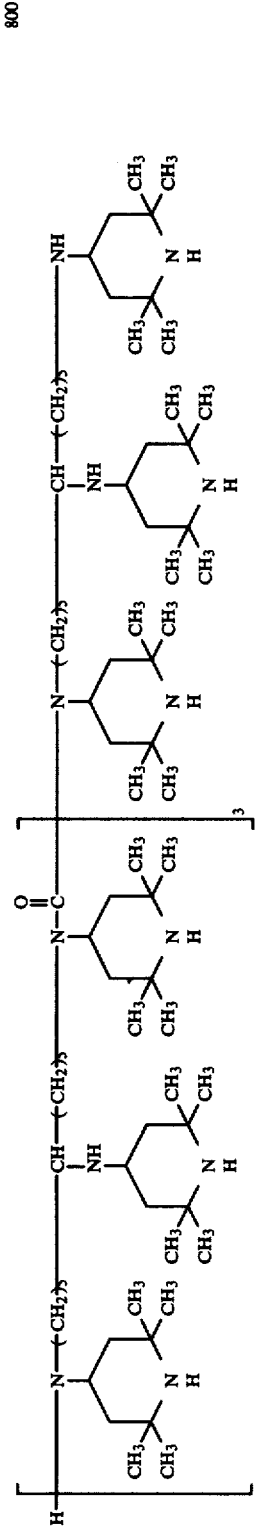 | 800 |
| Example 6 | 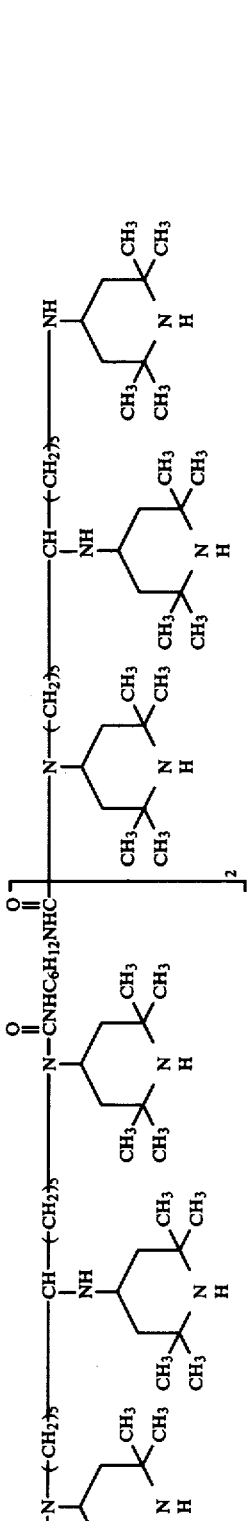 | 780 |
| Example 7 | | 860 |

TABLE I-continued

| Example No. | Stabilizer | Hours to Failure |
|---|---|---|
| Example 8 | | 540 |
| Example 9 | | 520 |
| Example 10 | | 610 |

TABLE I-continued

| Example No. | Stabilizer | Hours to Failure |
|---|---|---|
| Example 11 | (complex hindered phenol / tetramethylpiperidine structure) | 760 |
| Example 12 | (tris-substituted triazine with tetramethylpiperidinyl groups) | 790 |

The poly(piperidylamino)alkane stabilizers of the invention are clearly superior to the poly(piperidylamino)alkane stabilizers of the prior art.

EXAMPLES 13 TO 24

Conventional stabilizers for polymeric materials may lose their effectiveness because of volatilization or decomposition at high polymer processing temperatures. This is not true of the poly(piperidylamino)alkane stabilizers of the invention, as shown by observing the effect of heat in repeated extrusions of ethylene-propylene copolymer compositions. These compositions were prepared using stabilizers of the invention and of the prior art, and having the following formulation:

| Ingredient | Parts by Weight |
| --- | --- |
| Ethylene-propylene copolymer | 100 |
| Ca stearate | 0.2 |
| Stearyl-(3,5-di-t-butyl-4-hydroxyphenyl) propionate | 0.1 |
| Dilauryl thiodipropionate | 0.2 |
| Stabilizer as shown in Table II | 0.3 |

The ingredients were mixed and the compositions then extruded (cylinder temperature 230° C. and 240° C., head die temperature 250° C., velocity 20 rpm) three times. Test pieces were then molded by injection molding at 250° C. The test pieces were exposed to a high voltage mercury lamp, and the hours to failure noted as shown in Table II.

TABLE II

| Example No. | Stabilizer | Hours to Failure Extruded 1 time | Hours to Failure Extruded 3 times | % Retention of light stability |
|---|---|---|---|---|
| Control 1 | Polymer of 2,4-dichloro-6-n-butylamino-1,3,5-triazine with 1,6-bis(2,2,6,6-tetramethyl-4-piperidinylamino)hexane (M.W. = 3,000) | 400 | 290 | 73 |
| Control 2 | Polyamide of 1,6-bis(2,2,6,6-tetramethyl-4-piperidinylamino)hexane with adipic acid (M.W. = 2,500) | 360 | 240 | 67 |
| Control 3 | N,N'—distearoyl-N,N'—bis(2,2,6,6-tetramethyl-4-piperidinyl) ethylenediamine | 330 | 170 | 52 |
| Example 13 | [structure] | 690 | 630 | 91 |
| Example 14 | [structure] | 710 | 640 | 90 |
| Example 15 | [structure] | 780 | 740 | 95 |

TABLE II-continued

| | | Hours to Failure | | |
|---|---|---|---|---|
| Example No. | Stabilizer | Extruded 1 time | Extruded 3 times | % Retention of light stability |
| Example 16 | (structure) | 730 | 660 | 90 |
| Example 17 | (structure) | 740 | 680 | 96 |
| Example 18 | (structure) | 710 | 650 | 92 |

TABLE II-continued

| Example No. | Stabilizer | Hours to Failure | | % Retention of light stability |
|---|---|---|---|---|
| | | Extruded 1 time | Extruded 3 times | |
| Example 19 | (structure) | 820 | 770 | 94 |
| Example 20 | (structure) | 790 | 740 | 94 |
| Example 21 | (structure) | 610 | 530 | 87 |

TABLE II-continued

| Example No. | Stabilizer | Hours to Failure | | % Retention of light stability |
|---|---|---|---|---|
| | | Extruded 1 time | Extruded 3 times | |
| Example 22 | | 640 | 560 | 88 |
| Example 23 | | 680 | 610 | 90 |
| Example 24 | | 760 | 710 | 93 |

The poly(piperidylamino)alkane stabilizers of the invention are clearly superior to the poly(piperidylamino)alkane stabilizers of the prior art.

EXAMPLES 25 TO 36

High density polyethylene compositions were prepared using the stabilizers of the invention and two of the prior art, and having the following formulation:

| Ingredient | Parts by Weight |
| --- | --- |
| High-density polyethylene | 100 |
| Ca stearate | 1 |
| Tetrakis-(methylene-3-(3,5-di-t-butyl-4-hydroxyphenyl) propionate) methane | 0.1 |
| Distearylthiodipropionate | 0.3 |
| Stabilizer as shown in Table III | 0.2 |

The stabilizer was blended with the polymer on a two-roll mill, and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table III:

TABLE III
| Example No. | Stabilizer | Hours to Failure |
|---|---|---|
| Control 1 | Polymer of 2,4-dichloro-6-n-butylamino-1,3,5-triazine with 1,6-bis(2,2,6,6-tetramethyl-4-piperidinylamino) hexane (M.W. = 3,000) | 890 |
| Control 2 | N,N'—Distearoyl-N,N'—bis(2,2,6,6-tetramethyl-4-piperidinyl) ethylenediamine | 720 |
| Example 25 | 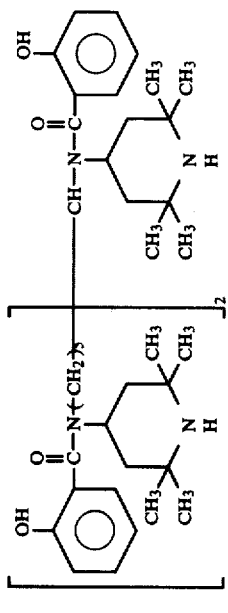 | 1,140 |
| Example 26 | 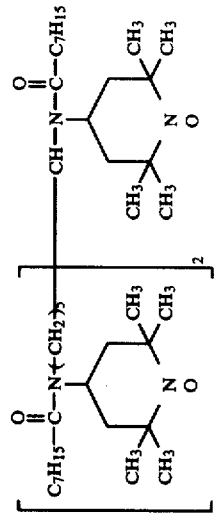 | 1,100 |
| Example 27 | 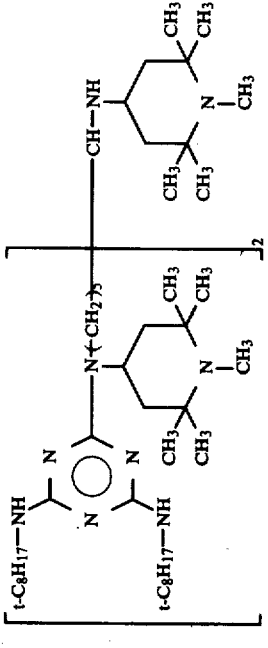 | 1,170 |

TABLE III-continued

| Example No. | Stabilizer | Hours to Failure |
|---|---|---|
| Example 28 | (structure) | 1,180 |
| Example 29 | (structure) | 1,220 |
| Example 30 | (structure) | 1,240 |

TABLE III-continued

| Example No. | Stabilizer | Hours to Failure |
|---|---|---|
| Example 31 | | 1,250 |
| Example 32 | | 1,070 |
| Example 33 | | 1,040 |
| Example 34 | | 1,090 |

TABLE III-continued
| Example No. | Stabilizer | Hours to Failure |
|---|---|---|
| Example 35 | 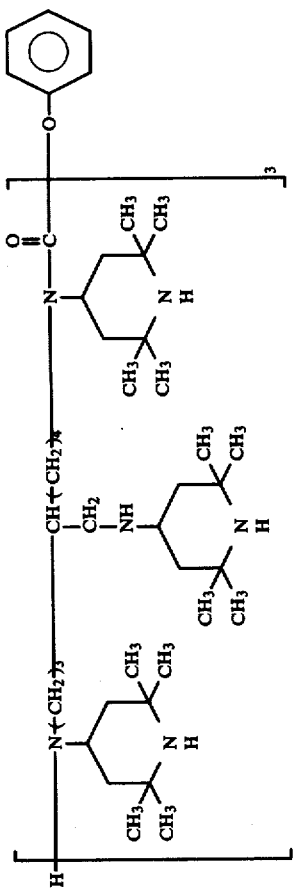 | 1,160 |
| Example 36 | 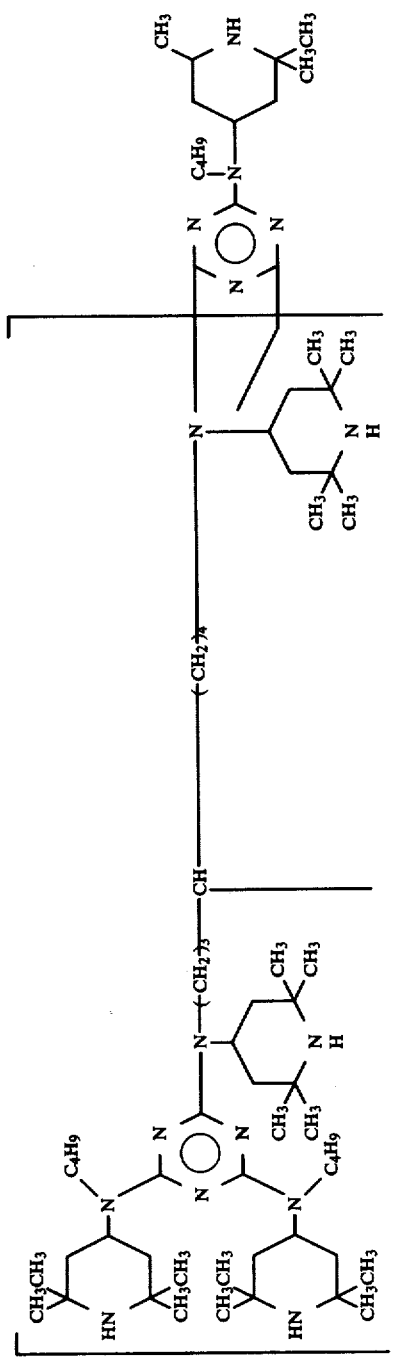 | |

The poly(piperidylamino)alkane stabilizers of the invention are clearly superior to the poly(piperidylamino)alkane stabilizers of the prior art.

EXAMPLES 37 TO 48

Ethylene-vinyl acetate copolymer compositions were prepared using stabilizers of the invention and three of the prior art, and having the following formulation:

| Ingredient | Parts by Weight |
|---|---|
| Ethylene-vinylacetate copolymer | 100 |
| 2,6-di-t-butyl-p-cresol | 0.1 |
| Ca stearate | 0.1 |
| Zn stearate | 0.1 |
| Diisodecylphenylphosphite | 0.2 |
| Stabilizer as shown in Table IV | 0.2 |

The stabilizer was blended with the polymer on a two-roll mill at 130° C., and sheets 0.4 mm thick were then compression-molded at 140° C. from the resulting blend. Pieces 2.5 cm square were cut off from the sheets and exposed to ultraviolet light in a Weather-O-Meter for 500 hours. At the start and at the conclusion of the test, the tensile strength of the sheet samples was determined. The results are shown in Table IV as % retention of the initially determined tensile strength.

TABLE IV

| Example No. | Stabilizer | % Retention of Tensile Strength After 500 Hours |
|---|---|---|
| Control 1 | Polymer of 2,4-dichloro-6-n-butylamino-1,3,5-triazine with 1,6-bis(2,2,6,6-tetramethyl-4-piperidinylamino) hexane (M.W. = 3,000) | 69 |
| Control 2 | N,N'—Distearoyl-N,N'—bis(2,2,6,6-tetramethyl-4-piperidinyl) ethylenediamine | 57 |
| Control 3 | N,N'—Bis(2,2,6,6-tetramethyl-4-piperidinyl)-N,N'—bis(β-3,5-di-t-butyl-4-hydroxypropionyloxyethyl)-1,6-hexanediamine | |
| Example 37 | 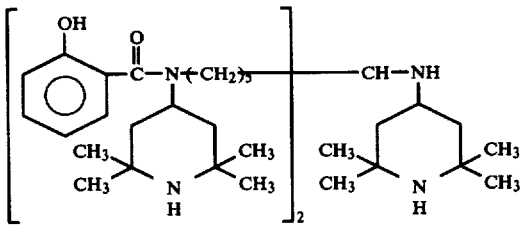 | 76 |
| Example 38 | 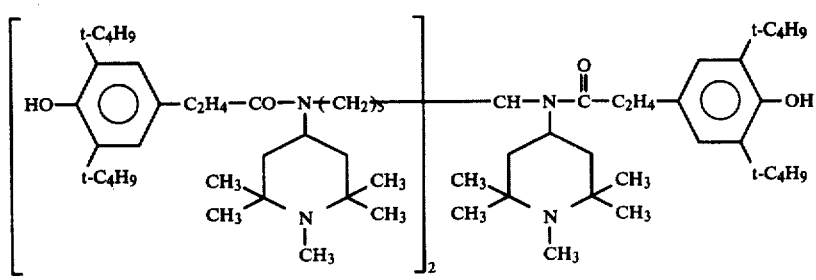 | 78 |
| Example 39 | 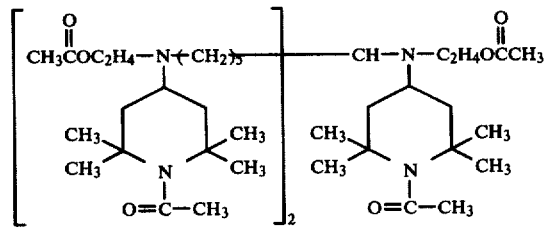 | 76 |

TABLE IV-continued

| Example No. | Stabilizer | % Retention of Tensile Strength After 500 Hours |
|---|---|---|
| Example 40 | (structure) | 81 |
| Example 41 | (structure) | 79 |
| Example 42 | (structure) | 84 |
| Example 43 | (structure) | 80 |

TABLE IV-continued
| Example No. | Stabilizer | % Retention of Tensile Strength After 500 Hours |
|---|---|---|
| | 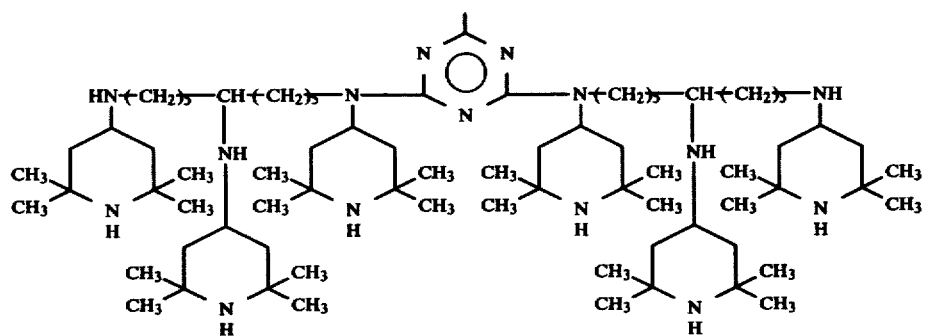 | |
| Example 44 | 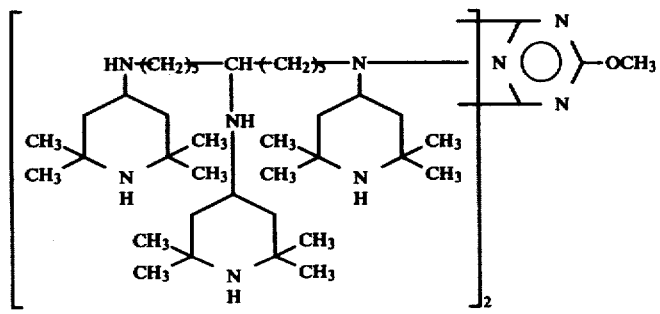 | 78 |
| Example 45 | 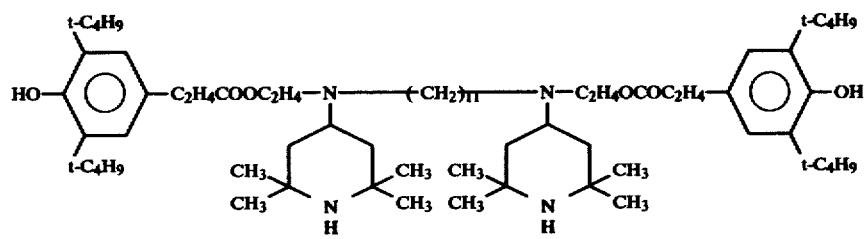 | 73 |
| Example 46 | 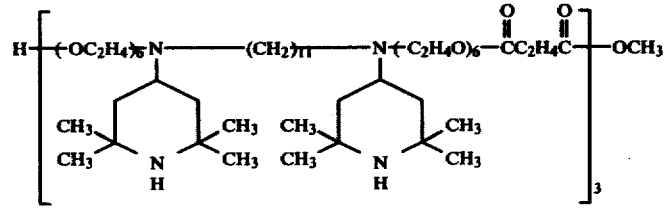 | 72 |
| Example 47 | 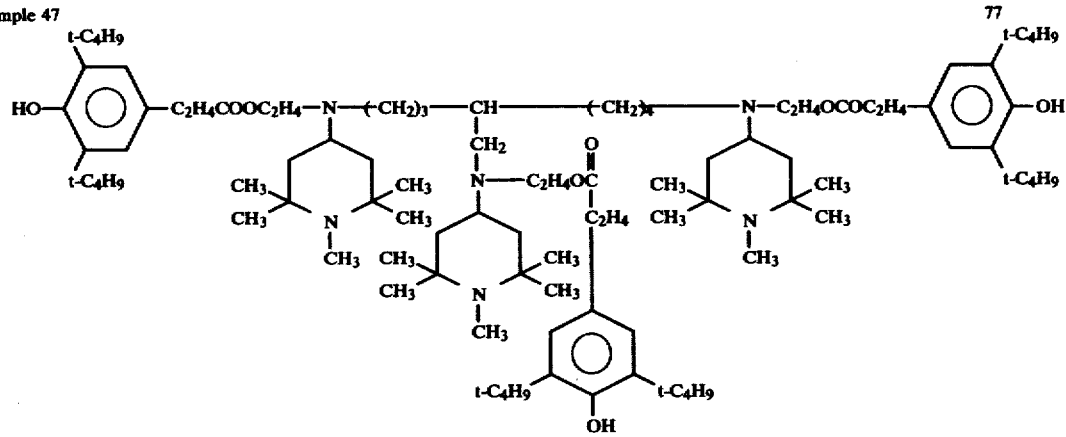 | 77 |

TABLE IV-continued

| Example No. | Stabilizer | % Retention of Tensile Strength After 500 Hours |
|---|---|---|
| Example 48 | | 81 |

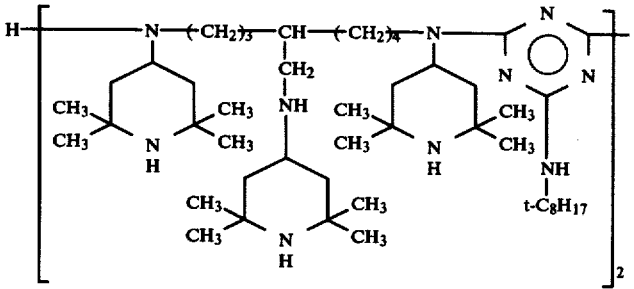

The poly(piperidylamino)alkane stabilizers of the invention are clearly superior to the poly(piperidylamino)alkane stabilizers of the prior art.

EXAMPLES 49 TO 60

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2 |
| Tris nonyl phenyl phosphite | 0.2 |
| Ca stearate | 1.0 |
| Zn stearate | 0.1 |
| Stabilizer as shown in Table V | 0.3 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light. The following results were obtained:

TABLE V

| Example No. | Stabilizer | Hours to Failure |
|---|---|---|
| Control 1 | None | 180 |
| Control 2 | Polymer of 2,4-dichloro-6-n-butylamino-1,3,5-triazine triazine with 1,6-bis(2,2,6,6-tetramethyl-4-piperidinylamino)hexane (M.W. = 3,000) | 550 |
| Example 49 | [structure] | 770 |
| Example 50 | [structure] | 750 |
| Example 51 | [structure] | 770 |
| Example 52 | [structure] | 780 |

TABLE V-continued
| Example No. | Stabilizer | Hours to Failure |
|---|---|---|
| Example 53 | 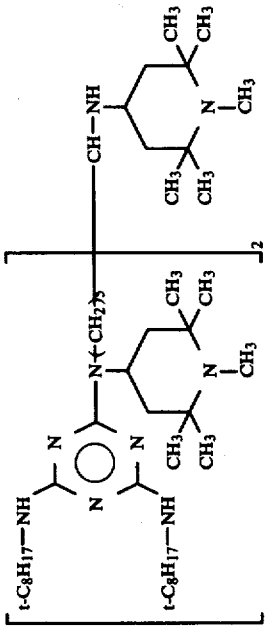 | 810 |
| Example 54 | 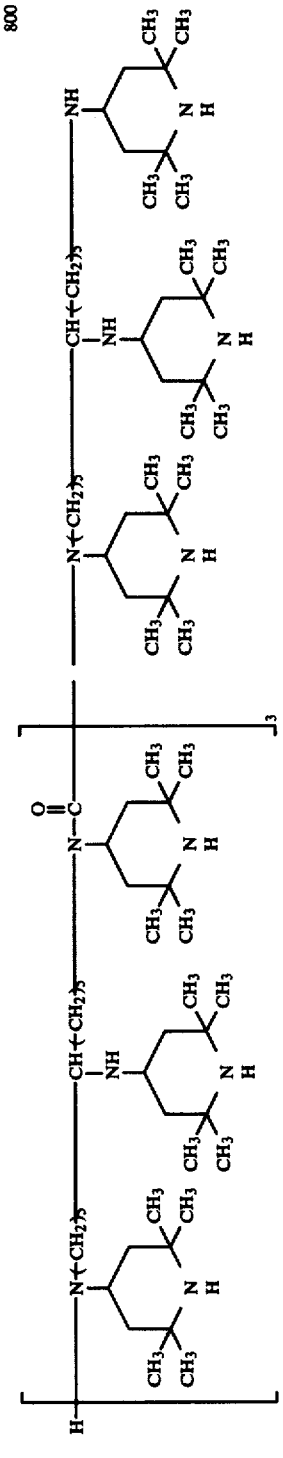 | 800 |
| Example 55 | 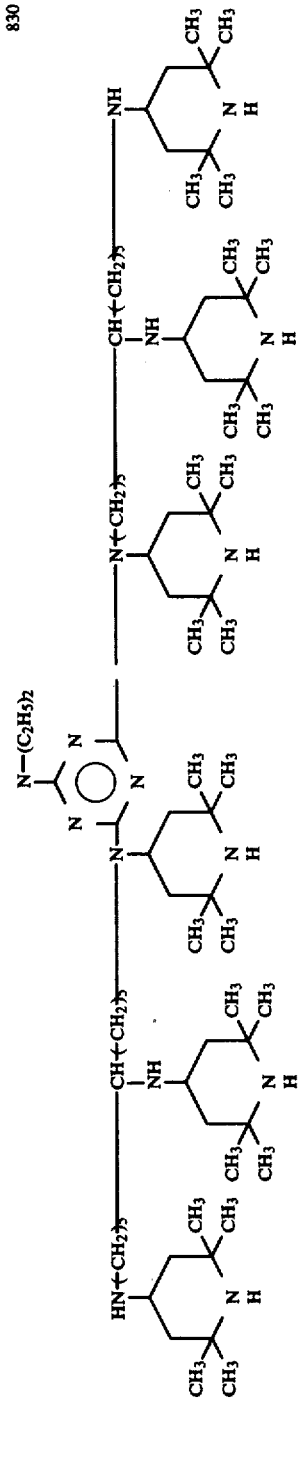 | 830 |

TABLE V-continued
| Example No. | Stabilizer | Hours to Failure |
|---|---|---|
| Example 56 | 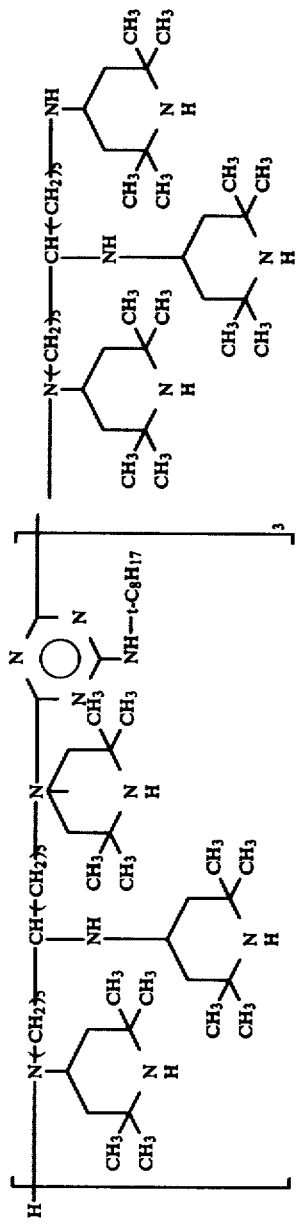 | 850 |
| Example 57 | 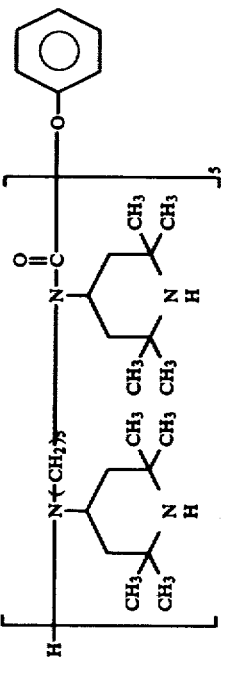 | 660 |
| Example 58 | 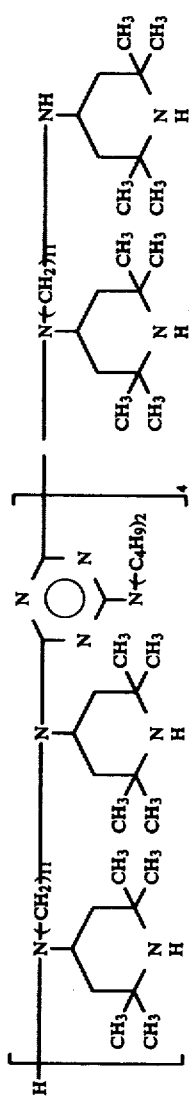 | |

TABLE V-continued

| Example No. | Stabilizer | Hours to Failure |
|---|---|---|
| Example 59 | (structure) | 780 |
| Example 60 | (structure) | 830 |

The poly(piperidylamino)alkane stabilizers of the invention are clearly superior to the poly(piperidylamino)alkane stabilizers of the prior art.

EXAMPLES 61 TO 72

Acrylonitrile-butadiene-styrene terpolymer resin compositions were prepared using stabilizers of the invention and two of the prior art, and having the following formulation:

| Ingredient | Parts by Weight |
| --- | --- |
| Acrylonitrile-butadiene-styrene terpolymer | 100 |
| 4,4'-butylidene-bis(2-tert-butyl-m-cresol) | 0.1 |
| Stabilizer as shown in Table VI | 0.3 |

The stabilizer was blended with the resin on a two-roll mill, and sheets 3 cm thick were prepared by compression molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table VI.

TABLE VI

| Example No. | Stabilizer | % Tensile Strength Retained |
|---|---|---|
| Control 1 | | 64 |
| Control 2 | | 59 |
| Example 61 | Polymer of 2,4-dichloro-6-n-butylamino-1,3,5-triazine with 1,6-bis(2,2,6,6-tetramethyl-4-piperidinylamino)hexane (M.W. = 3,000) N,N′—Distearoyl-N,N′—bis(2,2,6,6-tetramethyl-4-piperidinyl)ethylenediamine | 82 |
| Example 62 | | 84 |
| Example 63 | | 84 |

TABLE VI-continued

| Example No. | Stabilizer | % Tensile Strength Retained |
|---|---|---|
| Example 64 | (complex hindered amine structure) | 83 |
| Example 65 | (complex hindered amine structure) | 87 |
| Example 66 | (complex hindered amine structure) | 85 |

TABLE VI-continued

| Example No. | Stabilizer | % Tensile Strength Retained |
|---|---|---|
| Example 67 | (structure) | 83 |
| Example 68 | (structure) | 78 |
| Example 69 | (structure) | 77 |

TABLE VI-continued

| Example No. | Stabilizer | % Tensile Strength Retained |
|---|---|---|
| Example 70 | (structure) | 80 |
| Example 71 | (structure) | 83 |
| Example 72 | (structure) | 84 |

TABLE VI-continued
| Example No. | Stabilizer | % Tensile Strength Retained |
|---|---|---|
| | 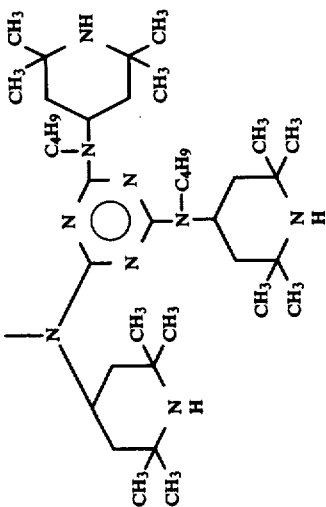 | |

The poly(piperidylamino)alkane stabilizers of the invention are clearly superior to the poly(piperidylamino)alkane stabilizers of the prior art.

EXAMPLES 73 TO 84

Polyurethane resin compositions were prepared using stabilizers of the invention and having the following formulation:

| Ingredient | Parts by Weight |
|---|---|
| Polyurethane resin (Asahi Denka[1] U-100) | 100 |
| Ba stearate | 0.7 |
| Zn stearate | 0.3 |
| 2,6-di-t-butyl-p-cresol | 0.1 |
| Stabilizer as shown in Table VII | 0.3 |

[1]A polyurethane-isocyanurate made from toluene diisocyanate and alkylene polyol.

The stabilizer was blended with the finely powdered polyurethane resin on a two-roll for five minutes at 70° C., and the sheet was then compression-molded at 120° C. for five minutes to form sheets 0.5 mm thick. Pieces 2.5 cm square were cut out from the sheets, and exposed to ultraviolet light in a Weather-O-Meter for thirty hours. Elongation before and after exposure was determined, and the percent elongation retained after the exposure is given in Table VII.

TABLE VII

| Example No. | Stabilizer | % Elongation Retention |
|---|---|---|
| Control 1 | Polymer of 2,4-dichloro-6-n-butylamino-1,3,5-triazine with 1,6-bis(2,2,6,6-tetramethyl-4-piperidinylamino)hexane (M.W. = 3,000) | 60 |
| Control 2 | N,N'—Distearoyl-N,N'—bis(2,2,6,6-tetramethyl-4-piperidinyl) ethylenediamine | 53 |
| Example 73 | 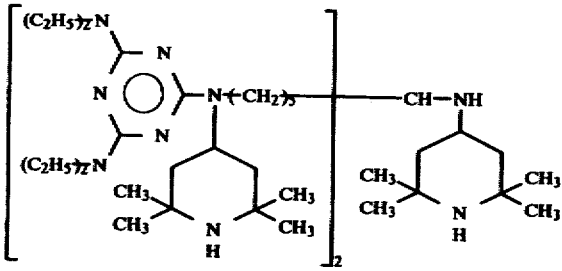 | 74 |
| Example 74 | 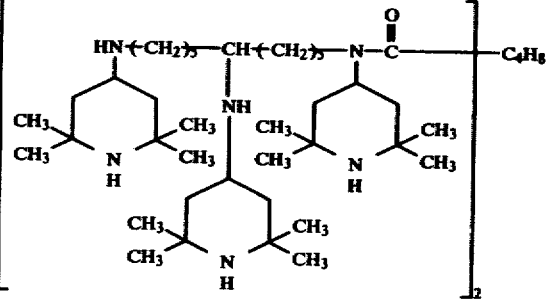 | 72 |
| Example 75 | 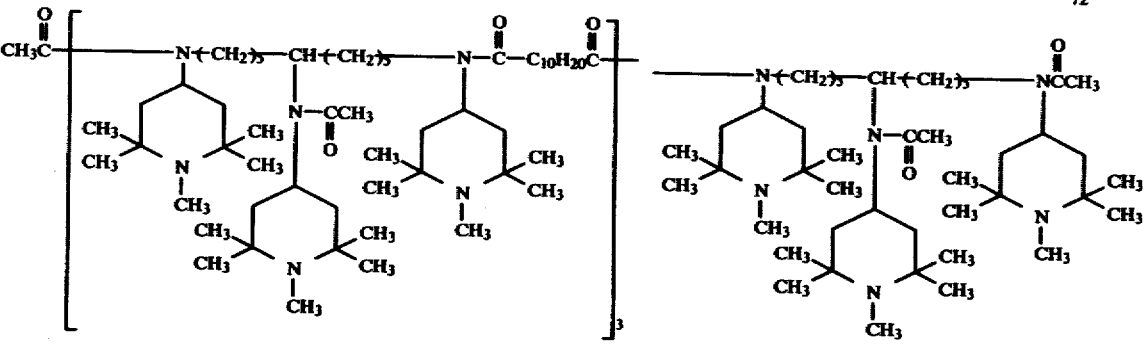 | 72 |
| Example 76 | | 73 |

TABLE VII-continued
| Example No. | Stabilizer | % Elongation Retention |
|---|---|---|
| Example 77 | 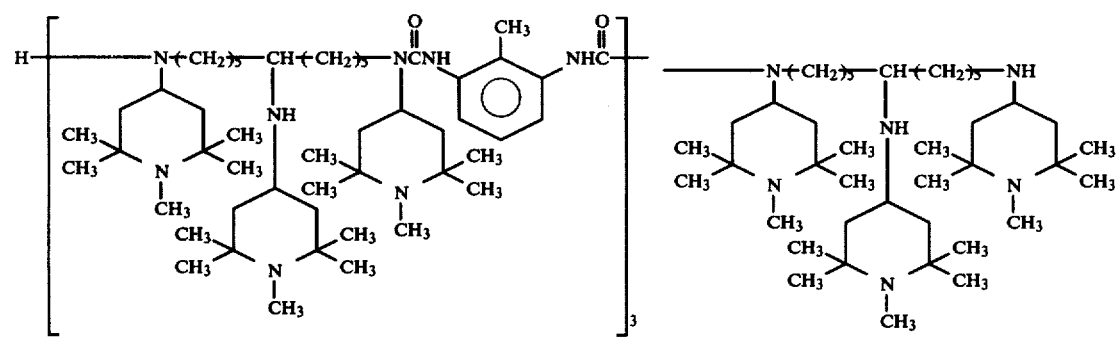 | 73 |
| Example 78 | 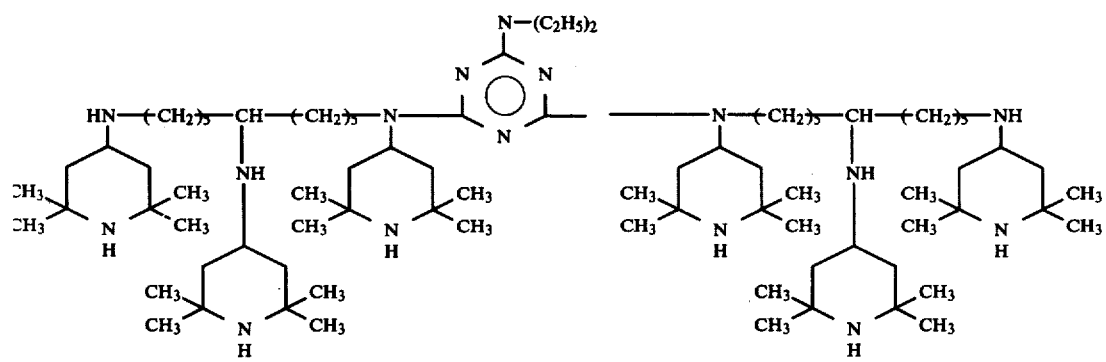 | 74 |
| Example 79 | 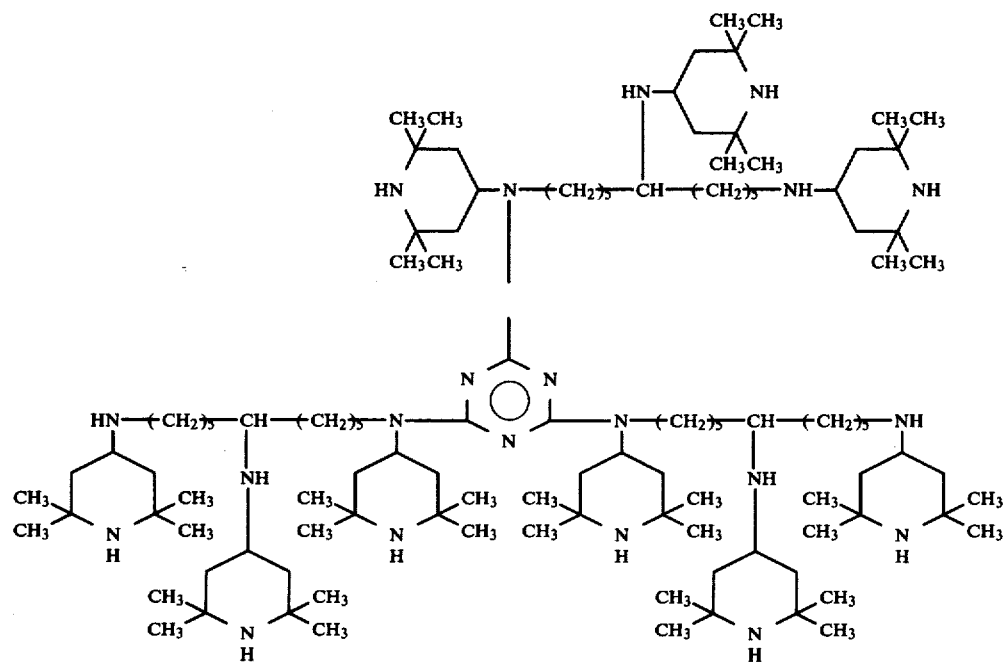 | 76 |

TABLE VII-continued

| Example No. | Stabilizer | % Elongation Retention |
|---|---|---|
| Example 80 | (structure) | 71 |
| Example 81 | (structure) | 72 |
| Example 82 | (structure) | 70 |
| Example 83 | (structure) | 73 |
| Example 84 | | 75 |

TABLE VII-continued

| Example No. Stabilizer | % Elongation Retention |
|---|---|

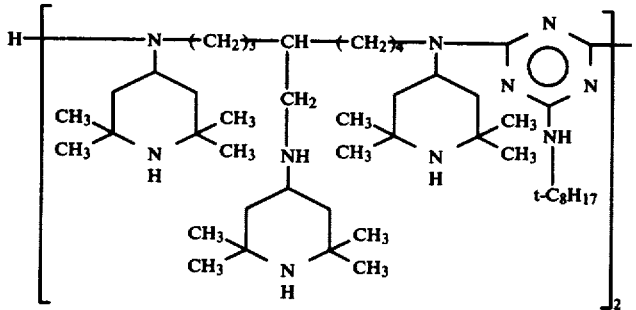

The poly(piperidylamino)alkane stabilizers of the invention are clearly superior to the poly(piperidylamino)alkane stabilizers of the prior art.

Having regard to the foregoing disclosure, the following is claimed as patentable and inventive embodiments thereof:

1. Poly-(2,2,6,6-tetramethylpiperidylamino)alkanes having the formula (I) or (II):

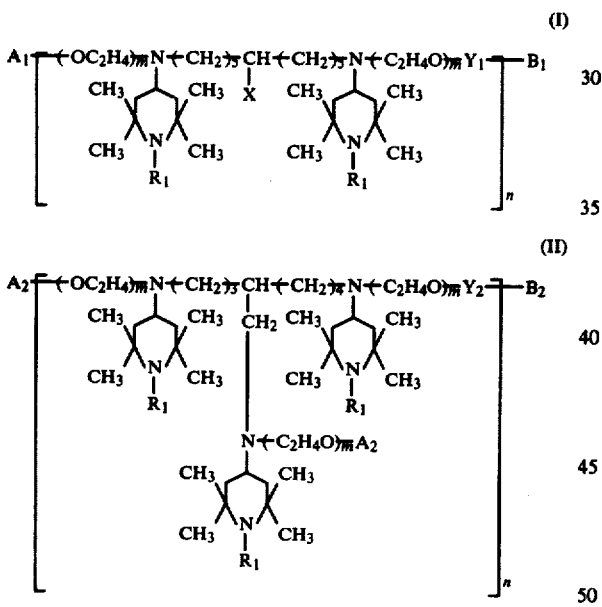

wherein:
X is hydrogen or

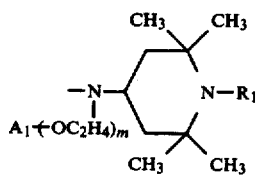

Y₁ is carbonyl

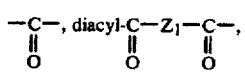

wherein $Z_1$ is a single bond; saturated or unsaturated alkylene having from one to twelve carbon atoms; or phenylene; dicarbamoyl

—CNHZ₂NHC—,
 ‖         ‖
 O         O where $Z_2$ is alkylene having from two to twelve carbon atoms; cyclohexylene and alkylcyclohexylene having five to ten carbon atoms; or phenylene and alkyl phenylene having six to twelve carbon atoms; diphenylene; diphenylene ether; diphenylene alkane, the alkane having one to four carbon atoms; or

$A_1$ is hydrogen, alkyl, hydroxyalkyl or epoxy alkyl having one to eighteeen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or $B_1$—$Y_1$—;

$B_1$ is —OR₂,

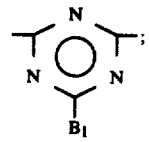

or

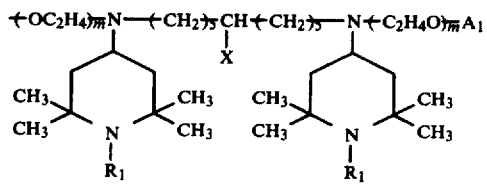

$Y_2$ is carbonyl

—C—, diacyl-C—Z₁—C—,
‖                ‖        ‖
O                O        O where $Z_1$ is a single bond; saturated or unsaturated alkylene having from one to twelve carbon atoms; or phenylene; dicarbamoyl

—CNHZ₂NHC—,
‖           ‖
O           O where $Z_2$ is alkylene having from two to twelve carbon atoms; cyclohexylene and alkylcyclohexylene having five to ten carbon atoms; or phenylene and alkyl phenylene having six to twelve carbon atoms; diphenylene, diphenylene ether; diphenylene alkane, the alkane having one to four carbon atoms; or

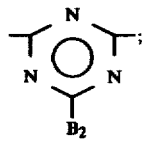

$A_2$ is hydrogen, alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or $B_2$—$Y_2$—;

$B_2$ is —$OR_2$—,

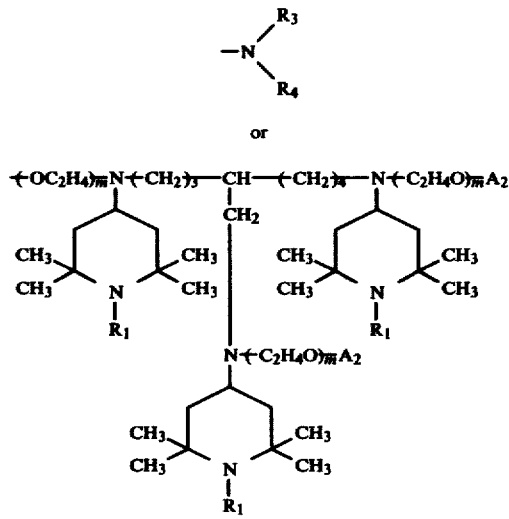

$R_1$ is hydrogen, alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkyhydroxyphenoyl having from six to ten carbon atoms or oxy;

$R_2$ is alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or aryl;

$R_3$ and $R_4$ each is hydrogen, alkyl, hydroxyalkyl or epoxy alkyl having one to eighteen carbon atoms; phenalkyl having from six to ten carbon atoms; alkanoyl having from two to eighteen carbon atoms; acryloyl; phenoyl, alkylphenoyl, hydroxyphenoyl and alkylhydroxyphenoyl having from six to ten carbon atoms or

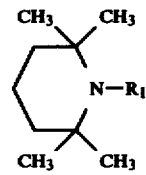

m is 0 to 10;
n is 1 to 20.

2. Poly(piperidylamine)alkanes according to claim 1 having the formula

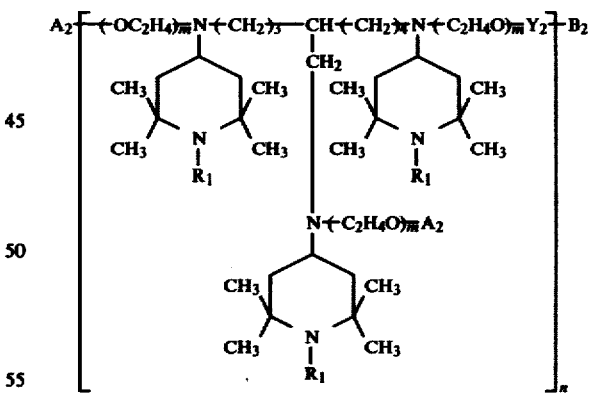

wherein:
$A_1$, $B_1$, $R_1$, X and $Y_1$ are as in claim 1.

3. Poly(piperidylamine)alkanes according to claim 1 having the formula

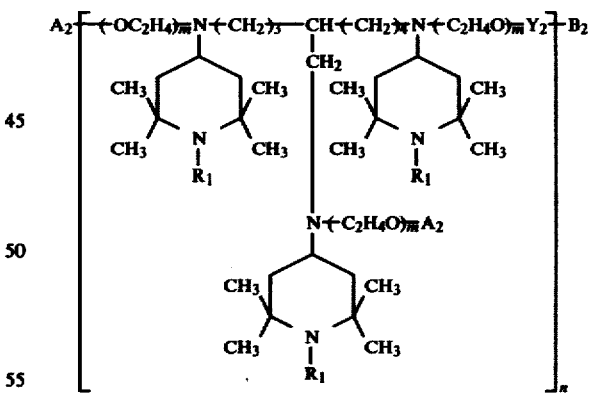

wherein:
$A_2$, $B_2$, $R_1$ and $Y_2$ are as in claim 1.

4. Poly(piperidylamine)alkane according to claim 1 wherein m is zero.

5. Poly(piperidylamine)alkane according to claim 1 wherein n is 1.

6. Poly(piperidylamine)alkane according to claim 1 wherein n is 2.

7. Poly(piperidylamine)alkane according to claim 1 wherein m is zero, n is 1, $R_1$ is hydrogen, $A_1$ is hydroxyphenoyl, $Y_1$ and $Y_2$ are C═O and $B_1$ is $R_2$.

8. Poly(piperidylamine)alkane according to claim 1 wherein m is zero, n is 1, $R_1$ is hydrogen, X is —N

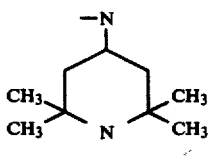

and $Y_1$ and $Y_2$ are

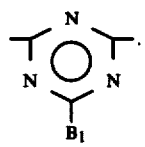

9. Poly(piperidylamine)alkane according to claim 1 wherein m is zero, $R_1$, X and $A_1$ are hydrogen, $Y_1$ is C=O and $B_1$ is

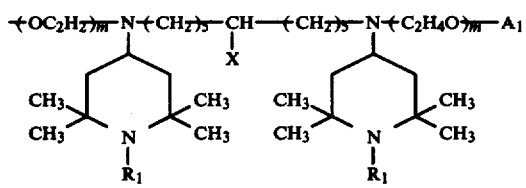

10. Poly(piperidylamine)alkane according to claim 1 wherein m is zero, $Y_1$ is

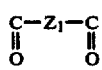

and $A_1$ is alkanoyl.

11. Poly(piperidylamine)alkane according to claim 1 wherein m is zero, $Y_1$ is and $B_1$ is

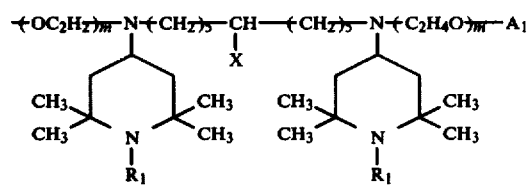

12. Poly(piperidylamine)alkane according to claim 1 wherein m is zero and $Y_1$ is

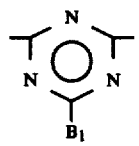

13. Poly(piperidylamine)alkane according to claim 1 wherein m is zero and $B_1$ is

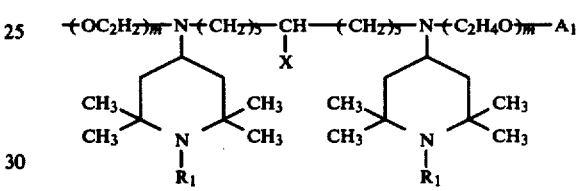

14. Poly(piperidylamine)alkane according to claim 1 wherein $Y_1$ is

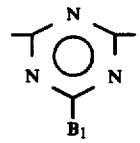

15. Poly(piperidylamine)alkane according to claim 1 having the structure:

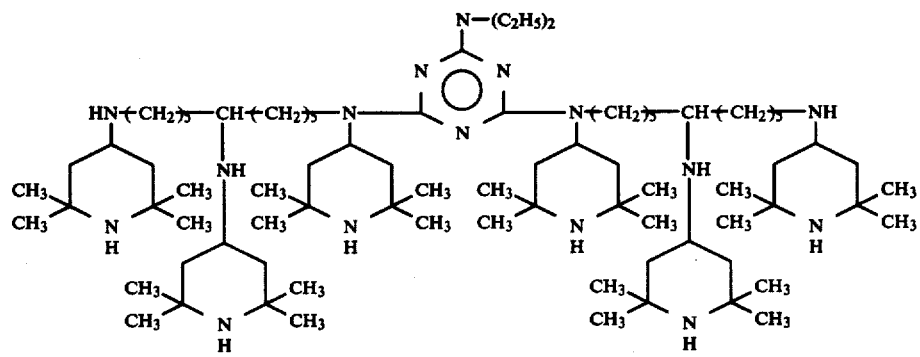

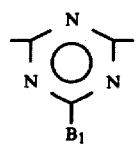

16. Poly(piperidylamine)alkane according to claim 1 having the structure:

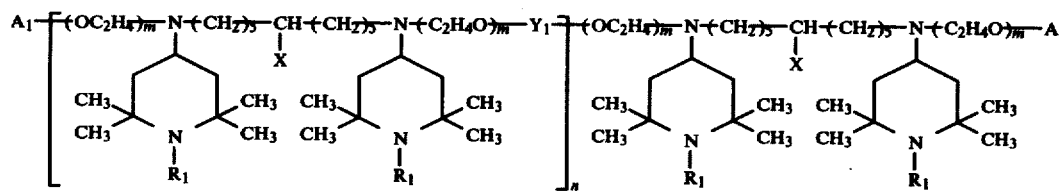
17. Poly(piperidylamine)alkane according to claim 1 having the structure:
18. Poly(piperidylamine)alkane according to claim 1 having the structure:
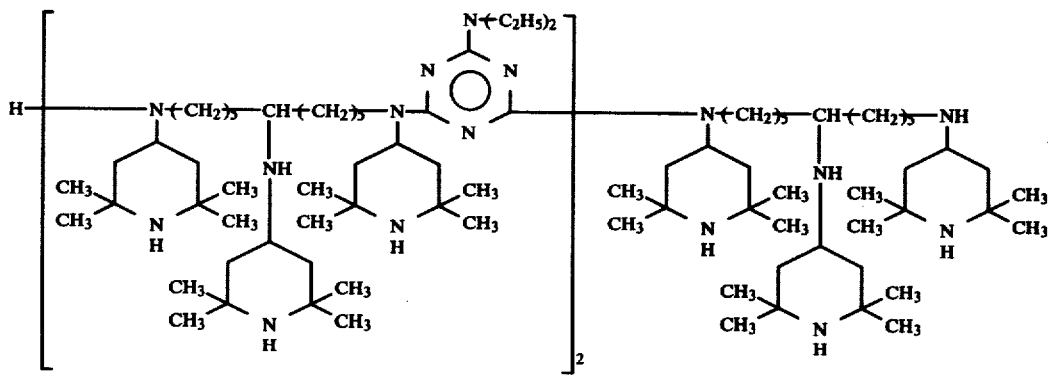
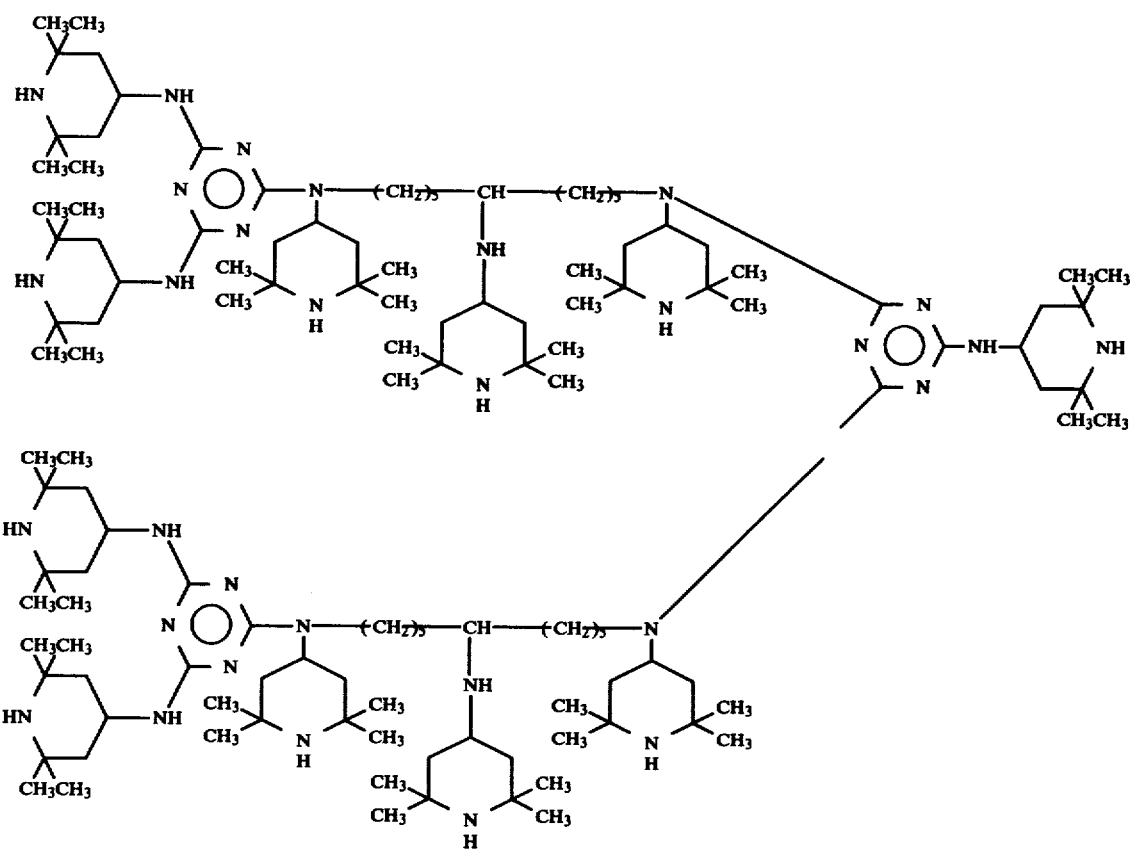
19. Poly(piperidylamine)alkane according to claim 1 having the structure:

20. Poly(piperidylamine)alkane according to claim 1 having the structure:

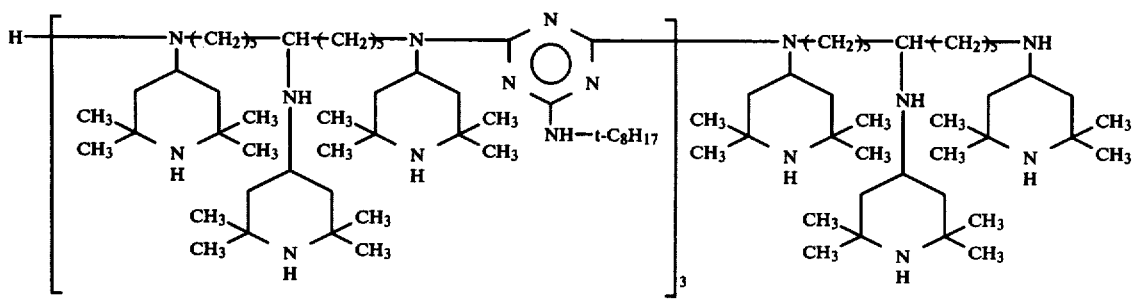

21. Poly(piperidylamine)alkane according to claim 1 having the structure:

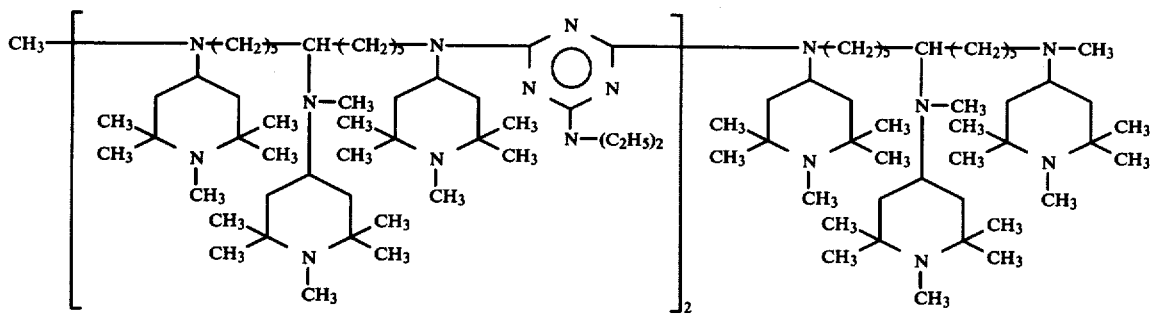

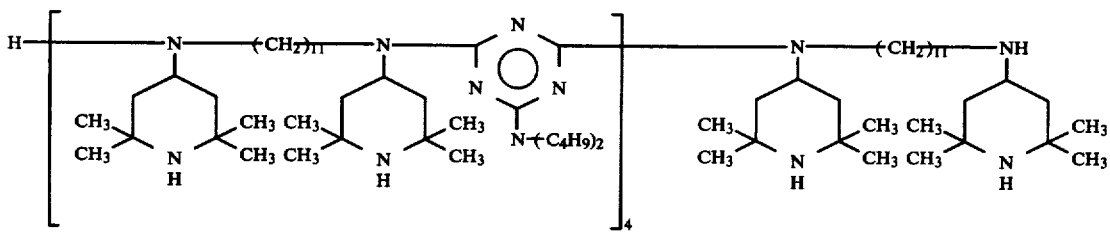

22. A polyvinyl chloride resin composition having improved resistance to deterioration upon exposure to light comprising a polyvinyl chloride resin formed at least in part of the recurring group:

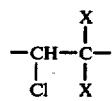

and having a chlorine content in excess of 40%, where X is either hydrogen or chlorine; and a compound in accordance with claim 1.

23. A polyvinyl chloride resin composition in accordance with claim 22 in which the polyvinyl chloride resin is polyvinyl chloride homopolymer.

24. A polyvinyl chloride resin composition in accordance with claim 22 in which the polyvinyl chloride resin is a copolymer of vinyl chloride and vinyl acetate.

25. An olefin polymer composition having improved resistance to deterioration upon exposure to light comprising an olefin polymer selected from the group consisting of polymers of alpha-olefins having from two to six carbon atoms and polystyrene, and a compound in accordance with claim 1.

26. An olefin polymer composition in accordance with claim 25 wherein the polyolefin is polypropylene.

27. An olefin polymer composition in accordance with claim 25 wherein the polyolefin is polyethylene.

28. An olefin polymer composition in accordance with claim 25 wherein the polyolefin is ethylene-propylene copolymer.

29. A polyurethane resin composition having improved resistance to deterioration upon exposure to light comprising a polyurethane resin and a compound in accordance with claim 1.

30. An ethylene-vinyl acetate copolymer composition having improved resistance to deterioration upon exposure to light comprising an ethylene-vinyl acetate copolymer and a compound in accordance with claim 1.

* * * * *